United States Patent
Xu et al.

(10) Patent No.: US 11,046,727 B2
(45) Date of Patent: Jun. 29, 2021

(54) METHODS FOR ISOLATION, IDENTIFICATION, AND QUANTIFICATION OF MIRNAS

(71) Applicant: LIFE TECHNOLOGIES CORPORATION, Carlsbad, CA (US)

(72) Inventors: Tom Xu, Castro Valley, CA (US); Christopher Trinh, San Jose, CA (US); Carole Bornarth, Fremont, CA (US); Brian Evans, Mountain View, CA (US); Mousumi Rath, San Ramon, CA (US); Kathy Tran, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/682,103

(22) Filed: Aug. 21, 2017

(65) Prior Publication Data

US 2018/0044371 A1 Feb. 15, 2018

Related U.S. Application Data

(62) Division of application No. 13/350,277, filed on Jan. 13, 2012, now abandoned.

(60) Provisional application No. 61/432,874, filed on Jan. 14, 2011.

(51) Int. Cl.
*C07H 21/02* (2006.01)
*C12Q 1/6876* (2018.01)
*C12N 15/10* (2006.01)
*C12Q 1/6809* (2018.01)
*C12Q 1/6834* (2018.01)

(52) U.S. Cl.
CPC ......... *C07H 21/02* (2013.01); *C12N 15/1006* (2013.01); *C12Q 1/6809* (2013.01); *C12Q 1/6834* (2013.01); *C12Q 1/6876* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 5,512,439 | A * | 4/1996 | Hornes | C12N 15/102 435/6.11 |
| 5,750,341 | A * | 5/1998 | Macevicz | C07H 21/02 435/6.19 |
| 2006/0057595 | A1 | 3/2006 | Lao et al. | |
| 2006/0099619 | A1 | 5/2006 | Remacle et al. | |
| 2007/0031865 | A1* | 2/2007 | Willoughby | C12N 15/1096 435/6.1 |
| 2007/0065844 | A1* | 3/2007 | Golub | C12Q 1/6834 435/6.14 |
| 2008/0076674 | A1* | 3/2008 | Litman | C12Q 1/6886 506/9 |
| 2008/0274904 | A1* | 11/2008 | Gormley | C12Q 1/6869 506/1 |
| 2010/0015604 | A1 | 1/2010 | Liandou et al. | |
| 2010/0209933 | A1 | 8/2010 | McReynolds et al. | |

FOREIGN PATENT DOCUMENTS

WO 2005/012523 2/2005

OTHER PUBLICATIONS

Sambrook et al. (2001) Molecular Cloning: A Laboratory manual,. 3rd ed. Cold Spring Harbor Laboratory Press, New York, pp. 9.55-9.56 (Year: 2001).*
Kuhn et al. (2005) Template-independent ligation of single-stranded DNA by T4 DNA ligase. FEBS Journal, 272:5991-6000 (Year: 2005).*
Gilad et al. (2008) Serum MicroRNAs Are Promising Novel Biomarkers. PLoS ONE, 3(9):e3148, pp. 1-7 (Year: 2008).*
Siva et al. (2009) Molecular assays for the detection of microRNAs in prostate cancer. Molecular Cancer, 8(17):pp. 1-12 (Year: 2009).*
Thompson et al. (1989) Enzymatic Amplification of RNA Purified from Crude Cell Lysate by Reversible Target Capture. Clinical Chemistry, 35(9): 1878-1881 (Year: 1989).*
Applied Biosystem's TaqMan MicroRNA Assays Protocol (2006), 36 pages (Year: 2006).*
Albretsen, C. et al. "Applications of Magnetic Beads with Covalently Attached Oligonucleotides in Hybridization: Isolation and Detection of Specific Measles Virus mRNA from a Crude Cell Lysate", Analytical Biochemistry, Mar. 16, 1990, 40-50.
Biscontin, et al., "New miRNA labeling method for bead-based quantification", BMC Molecular Biology, vol. 11:44, Jun. 16, 2010, p. 7.
Castoldi, et al., "How to Assay microRNA ExpressioExpression; A Technology Guide", Regulation of Gene Expression by Small RNAs, Chapter 12, 2009, 215-240.
Chen, et al., "Highly sensitive and specific microRNA expression profiling using BeadArray technology", Nucleic Acids Research, vol. 36, No. 14, 2008, pp. e87-e87.
Chen, Patrick, "Identification of Dysregulated miRNA in Targets in Human Prostate Cancer", A Dissertation, Approved by the Institute of Biomedical Studies, Dec. 2009, 107 Pgs.
El-Khoury, Victoria, et al., "Assessing cellular and circulating miRNA recovery: the impact of the RNA isolation method and the quantity of input material", Scientific Reports, Jan. 20, 2016, 1-14.
EP12757380, Supplementary Partial European Search Report dated Jan. 12, 2015, 7 pages.
EP12757380.6, Extended European Search Report dated May 18, 2015, 11 Pages.
EP17190361, Partial European Search Report dated Dec. 12, 2017, 1-18 pages.

(Continued)

*Primary Examiner* — Neil P Hammell

(57) ABSTRACT

Method and compositions and kits for isolation, identification, and quantification of miRNAs and other small RNAs, including but not limited to, siRNAs, mRNAs, and snRNAs are disclosed. Methods of diagnosing a disease or its progression are also disclosed.

17 Claims, 20 Drawing Sheets

Specification includes a Sequence Listing.

(56) References Cited

OTHER PUBLICATIONS

Flagella, et al., "A multiplex branched DNA assay for parallel quantitative gene expression profiling", Analytical Biochemistry, 2006, 352:50-60.

Gilad, et al., "Serum MicroRNAs Are Promising Novel Biomarkers", PLoS ONE, 3(9):e3148, 2008, 1-7.

Huang, et al., "Bead-based microarray analysis of microRNA expression in hepatocellular carcinoma: miR-338 is downregulated", Hepatology Research, vol. 39, 2009, 786-794.

Kroh, Evan, et al., "Analysis of circulating microRNA biomarkers in plasma and serum using quantitative reverse transcription-PCR (qRT-PCR)", Methods, 2010, 298-301.

Kuhn, et al., "Template-independent ligation of single-stranded DNA by T4 DNA ligase", FEBS Journal, 2005, 272:5991-6000.

Lee; Hyewon, et al., "Encoded Hydrogel Microparticles for Sensitive and Multiplex microRNA Detection Directly from Raw Cell Lysates", Analytical Chemistry, Mar. 15, 2016, 3075-3081.

Lu, et al., "MicroRNA expression profiles classify human cancers", Nature, vol. 435, No. 7043, 2005, 834-838.

PCT/US2012/021264, International Search Report and Written Opinion dated Aug. 24, 2012, 12 Pages.

Podolska, Agnieszka, et al. "How the RNA isolation method can affect microRNA microarray results", Acta Biochimica Polonica, Dec. 6, 2011, 1-6.

Sambrook, et al., "Molecular Cloning: A Laboratory manual", 3rd ed. Cold Spring Harbor Laboratory Press, 2001, 9.55-9.56.

Shi, et al., "Facile Means for Quantifying MicroRNA Expression by Real-Time PCR", Biotechniques, vol. 39, No. 4, 2005, 519-525.

Siva, et al., "Molecular assays for the detection of microRNAs in prostate cancer", Molecular Cancer, 8(17), 2009, 1-12.

Thompson, et al., "Enzymatic Amplification of RNA Purified from Crude Cell Lysate by Reversible Target Capture", Clinical Chemistry, 35(9), 1989,1878-1881.

Tong, et al., "MicroRNA profile analysis of human prostate cancers", Cancer Gene Therapy, vol. 16, No. 3, 2009, 206-216.

Wang, Wang-Xia, et al., "Focus on RNA isolation: Obtaining RNA for microRNA (miRNA) expression profiling analyses of neural tissue", Biochimica Et Biophysica Acta., Nov. 1, 2008, 749-757.

Extended European Search Report for Application No. 17190361, dated Mar. 21, 2018, 15 pages.

EP20169178.9, Extended European Search Report, dated Jan. 13, 2021, 17 pages.

EP20169178.9, Partial European Search Report, dated Sep. 24, 2020, 18 pages.

* cited by examiner

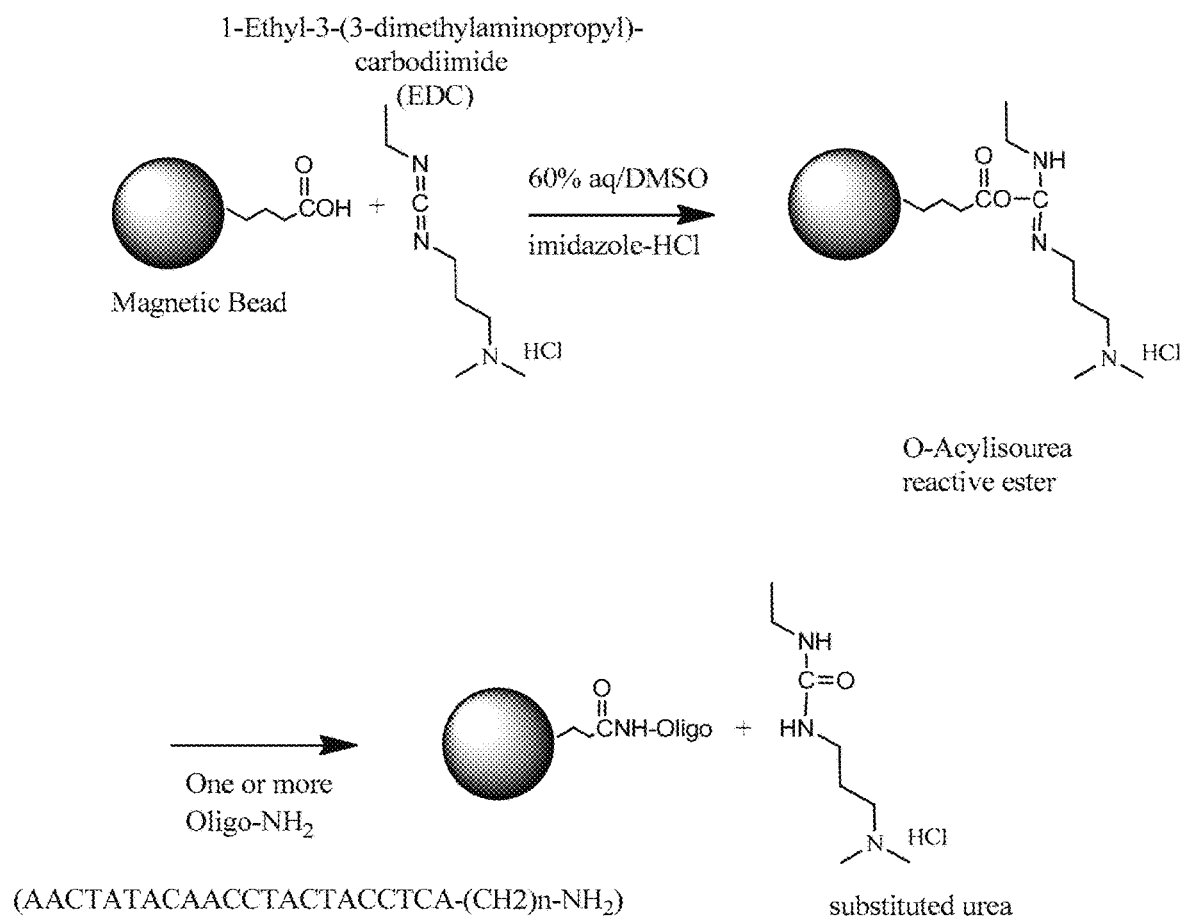
FIG. 1: Schematic for making anti-miRNA probe beads using chemical synthesis

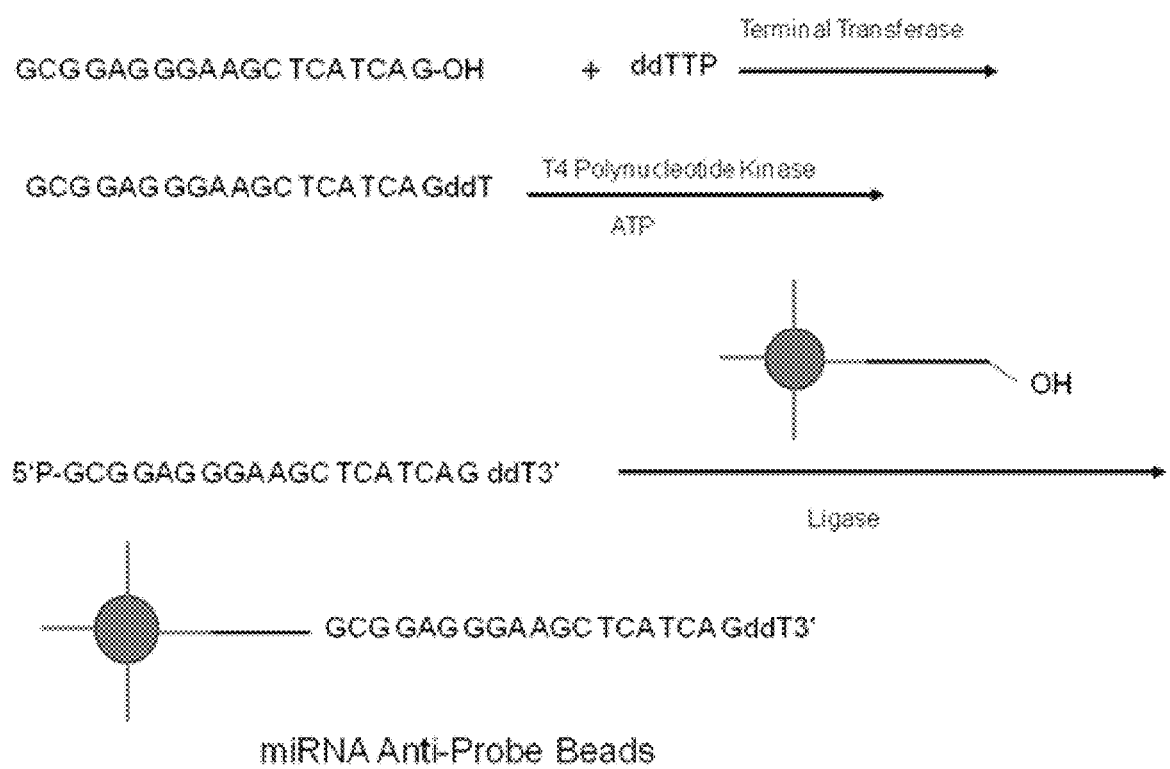
FIG. 2: Schematic for enzymatic synthesis of anti-miRNA probe beads

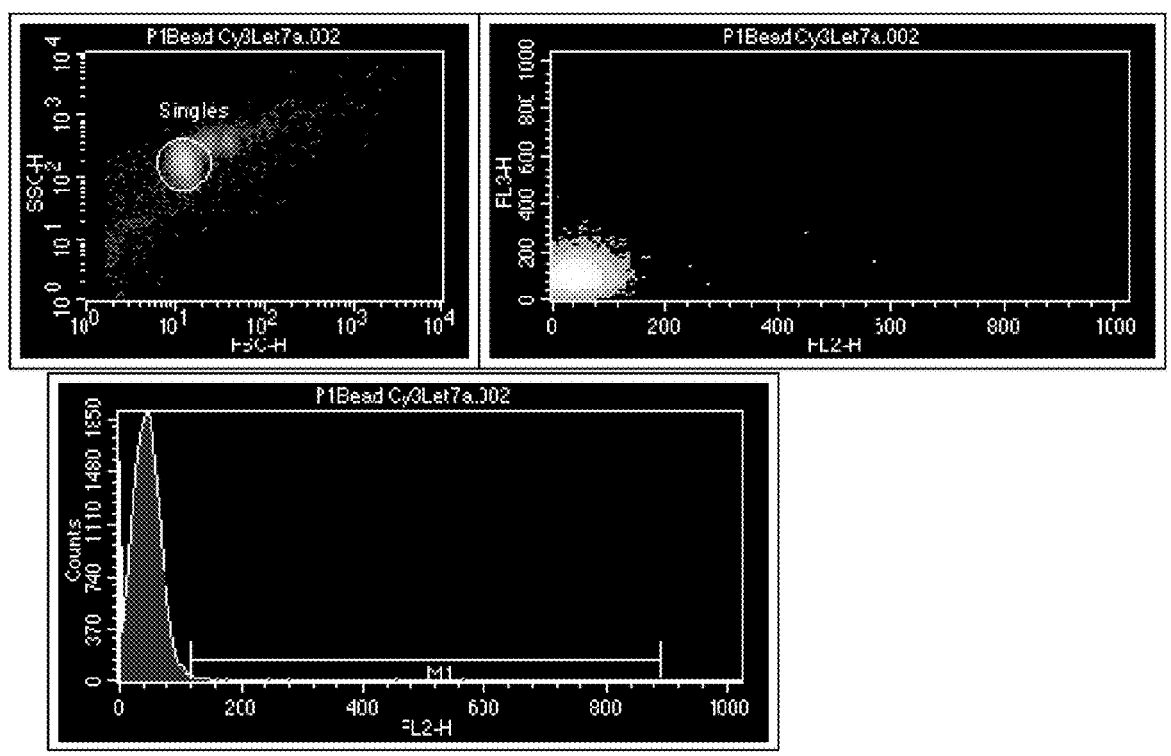
FIG. 3A: Non-anti-probe beads hybridization with Cy3-laneled Let-7a

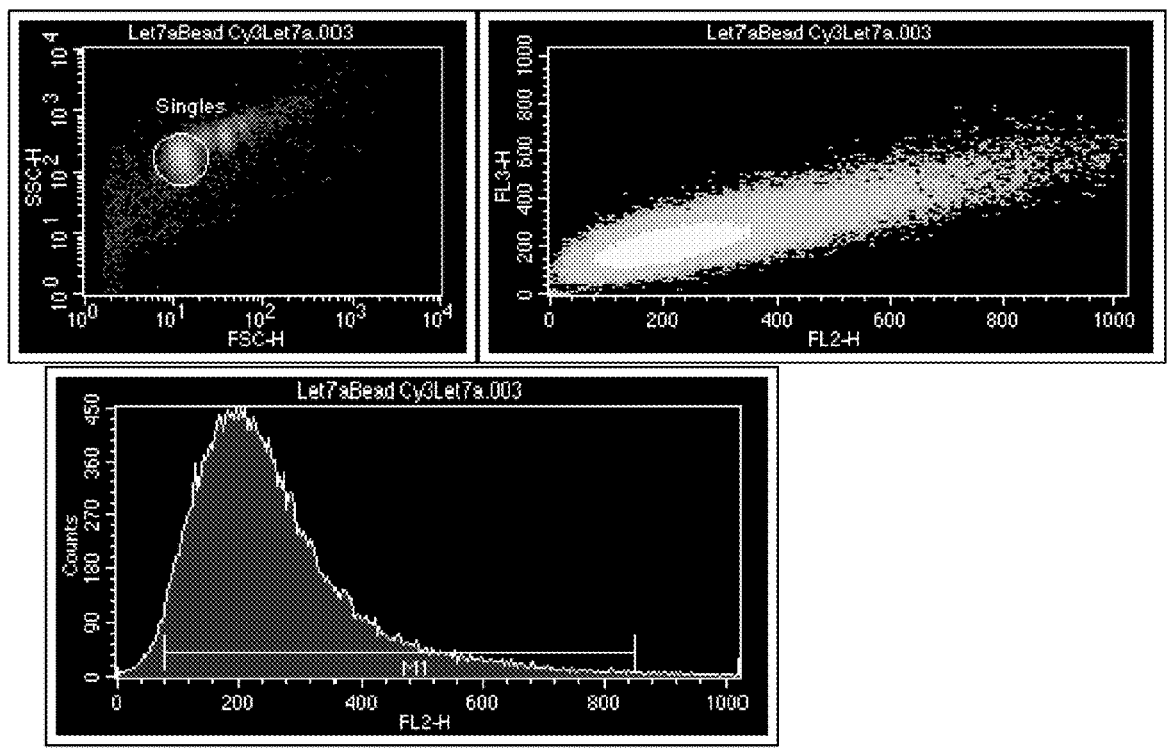
FIG. 3B: Anti-Let-7a-probe beads hybridization with Cy3-labeled Let-7a

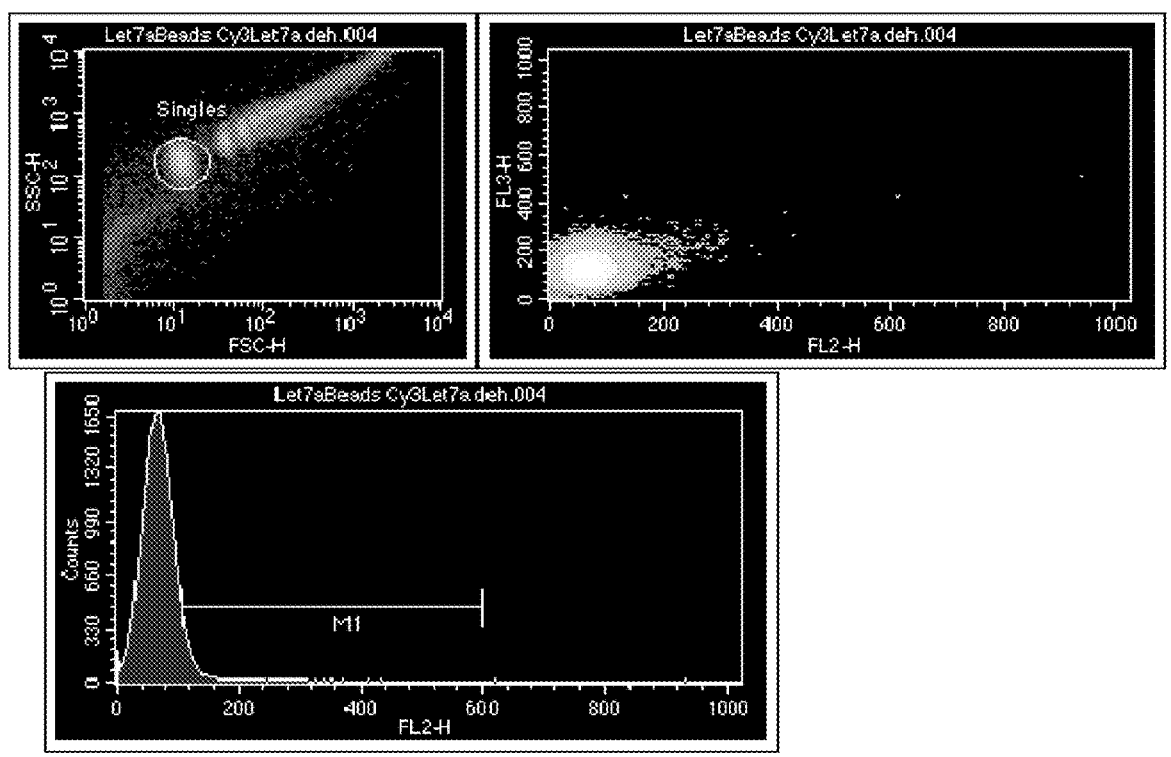
FIG. 3C: FACS after de-hybridization of Cy3-labeled Let-7a bond from anti-Let-7a-probe beads

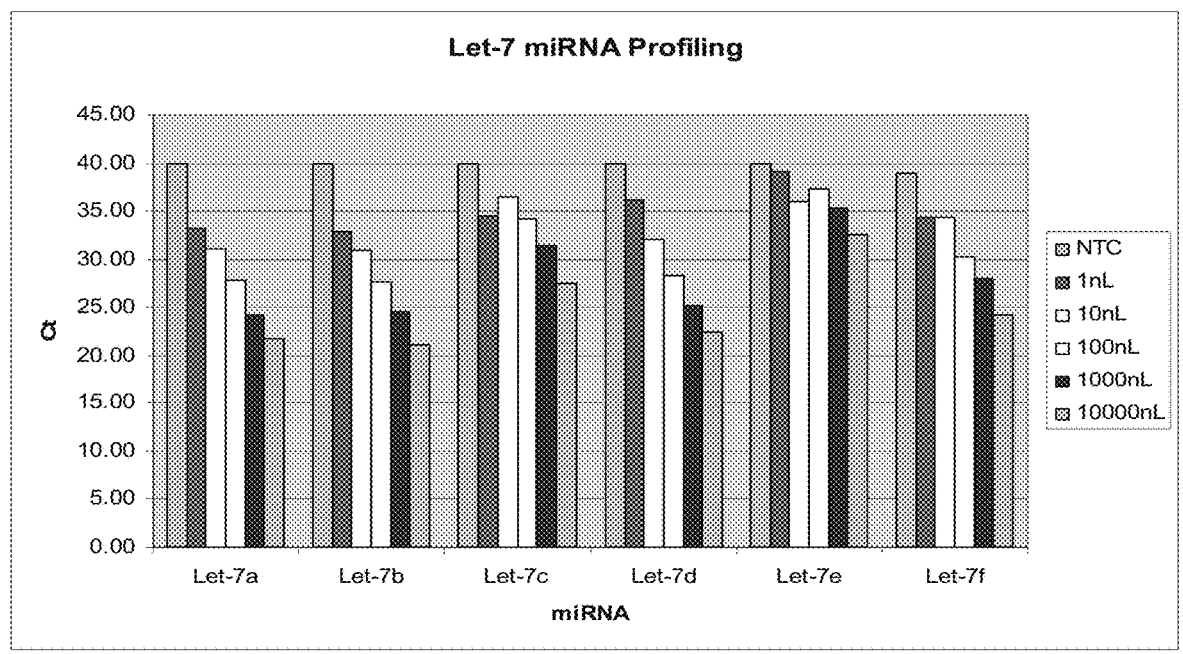
FIG. 4: Let-7 family miRNA profiling by Ct values

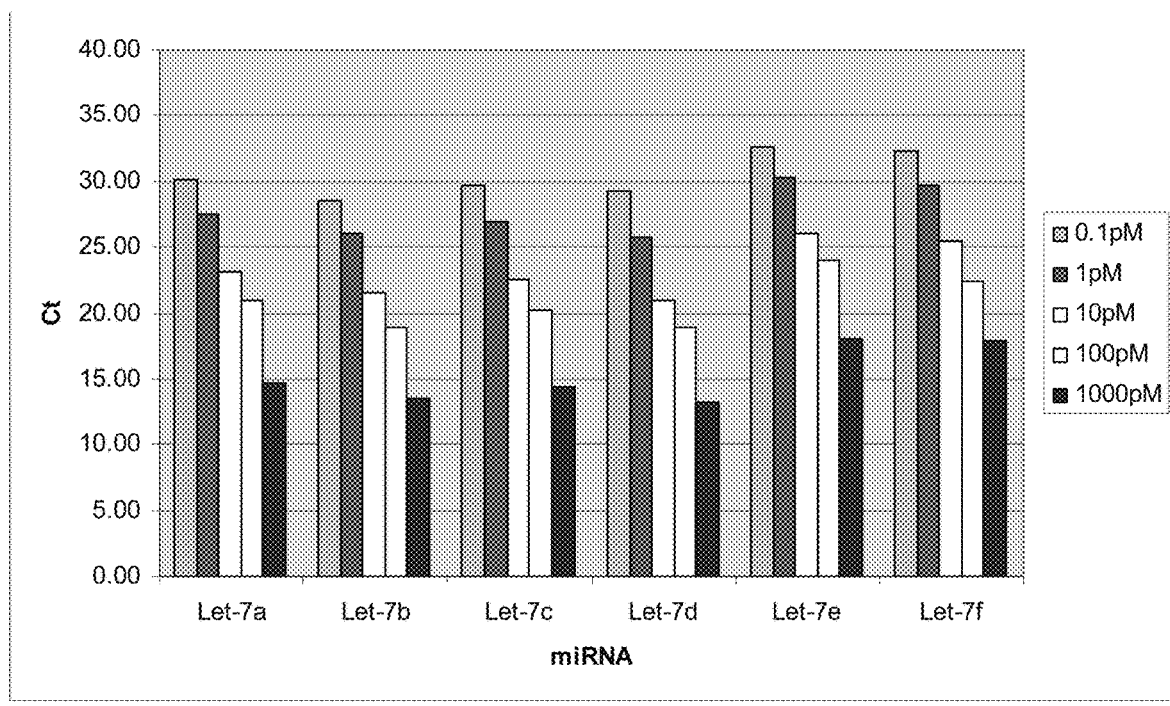
FIG. 5: miRNA detection after addition (spiking) to plasma

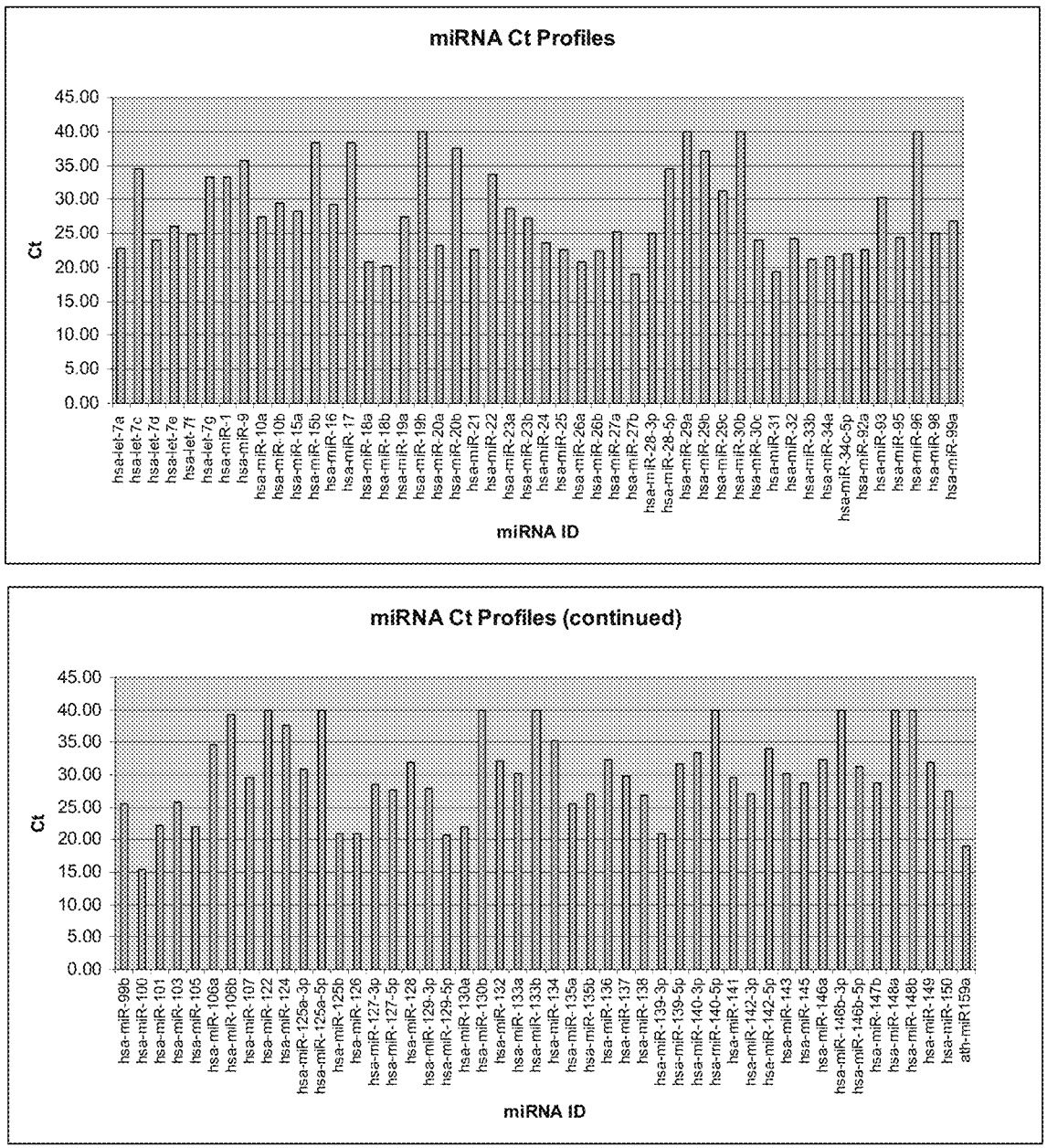
FIG. 6A: 96 miRNA profiling using anti miRNA beads

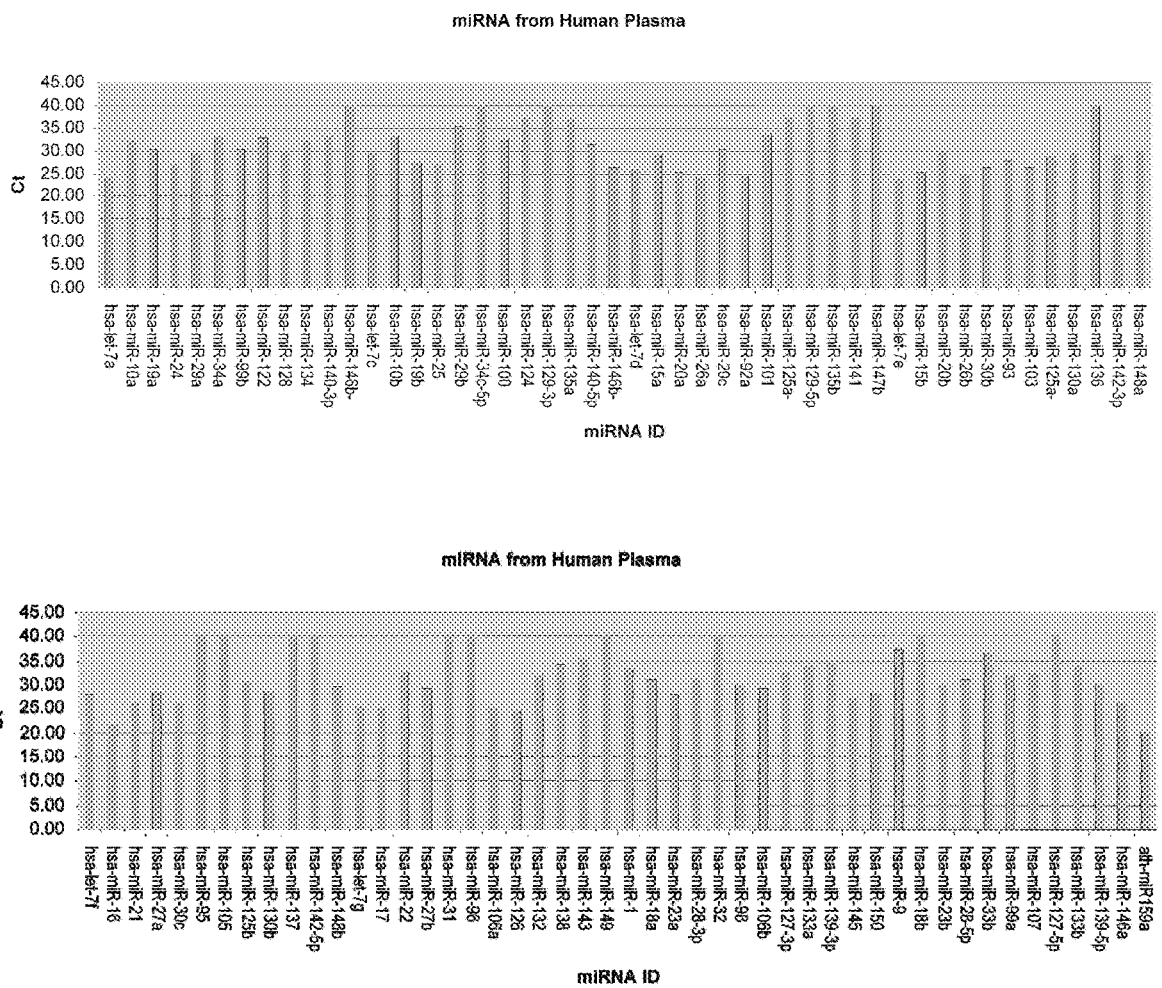
FIG. 6B: Quantitative real-time PCR Ct profiles of 95 miRNAs from blood

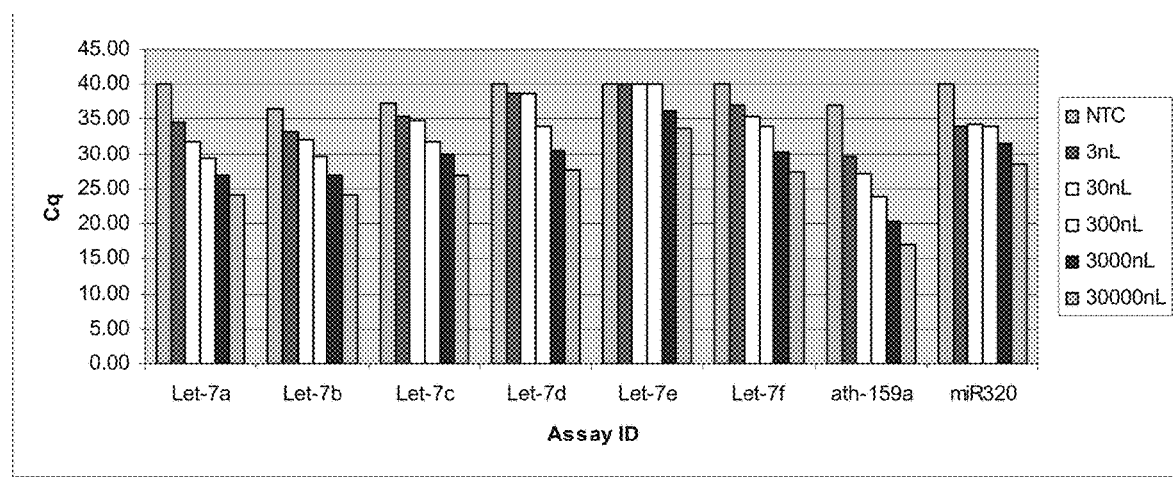
FIG. 7: Saliva miRNA profiling using anti-miRNA probe beads

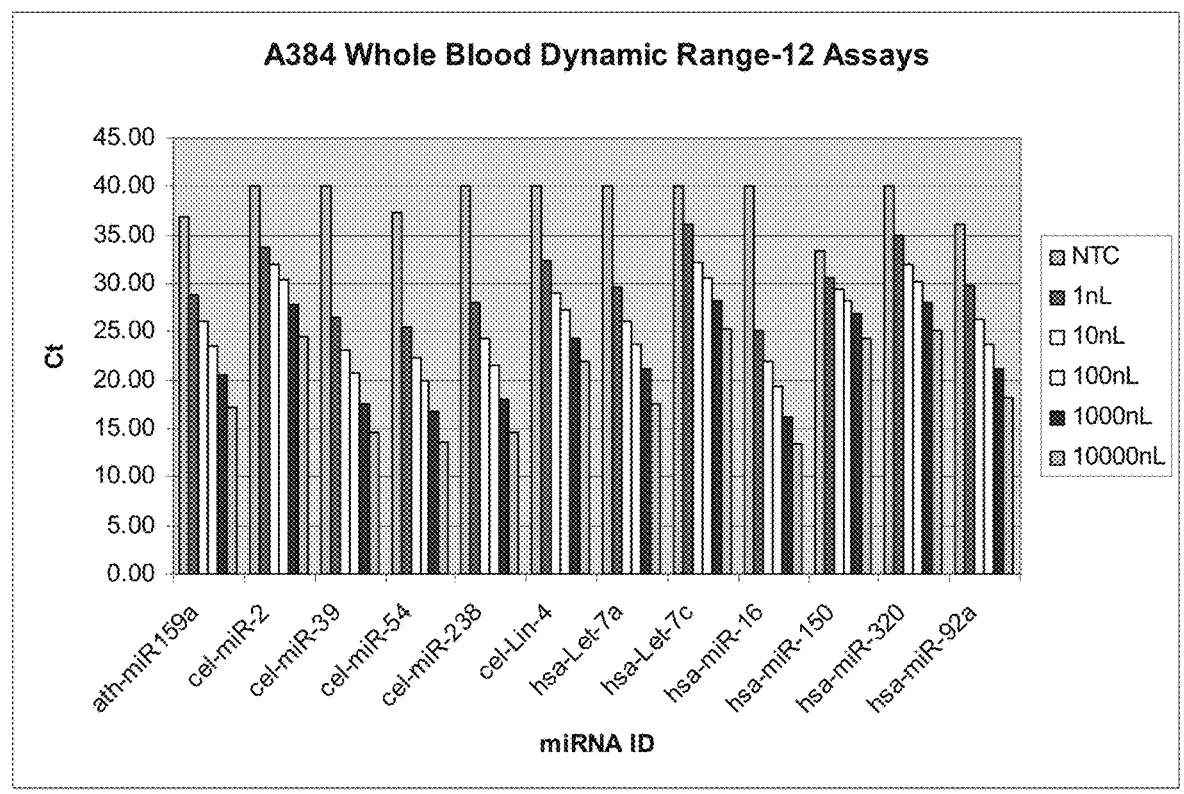
FIG. 8: A384C6 Beads Sensitivity and Dynamic Range

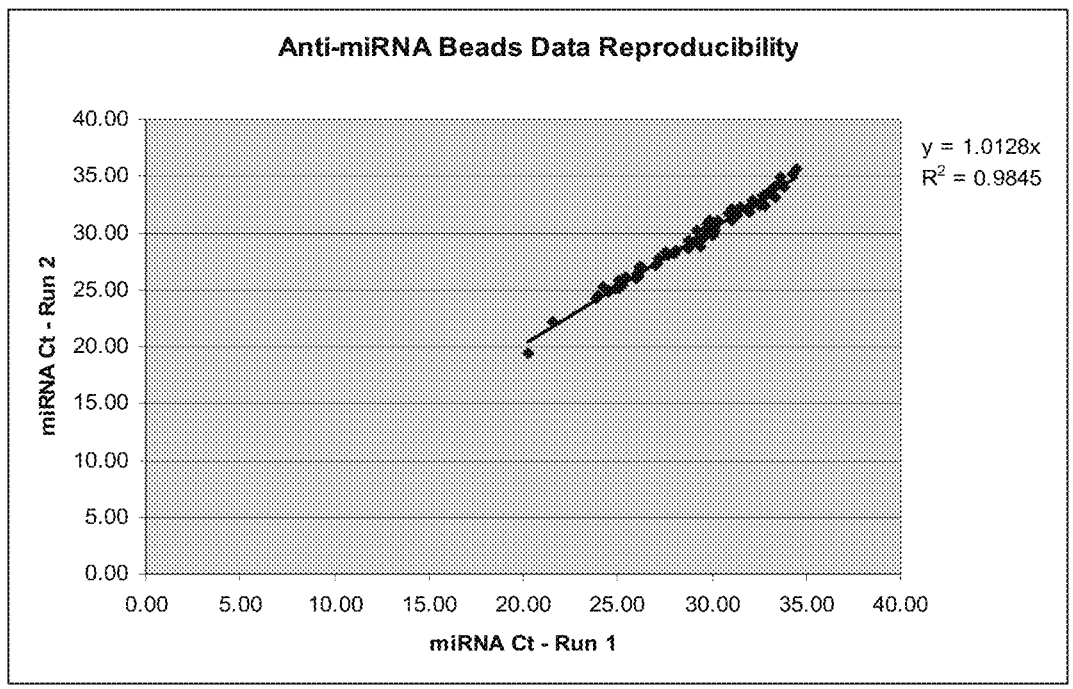
FIG. 9: miRNA Detectability and reproducibility.
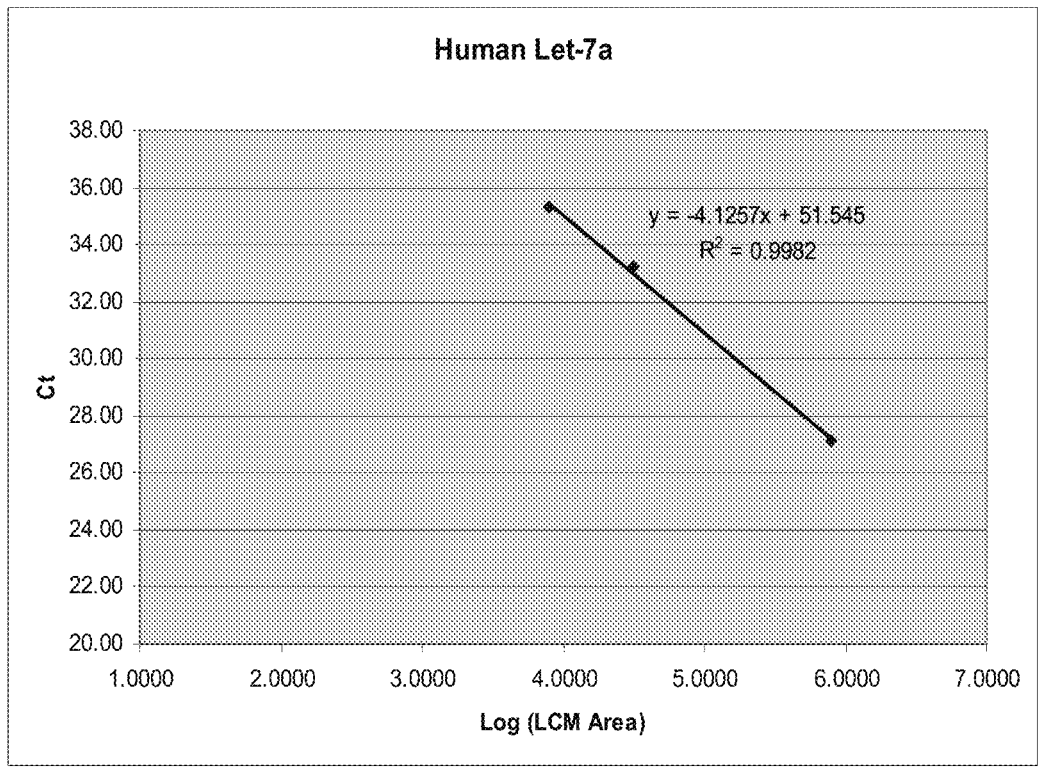
FIG. 10A: Let7a - miRNA profiling from human bladder LCM samples; LCM area and Ct correlation

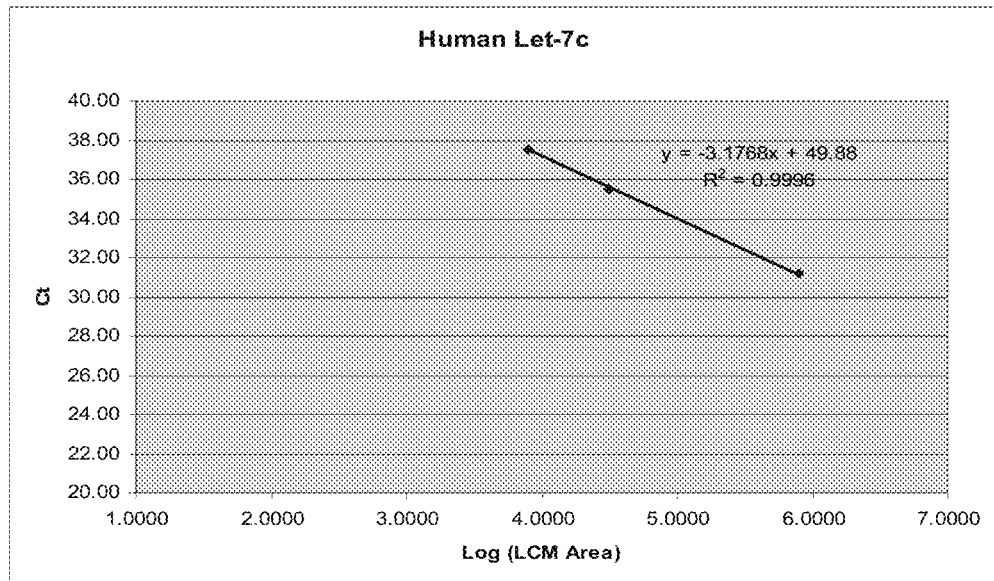
FIG. 10B: Let7c - miRNA profiling from human bladder LCM samples; LCM area and Ct correlation
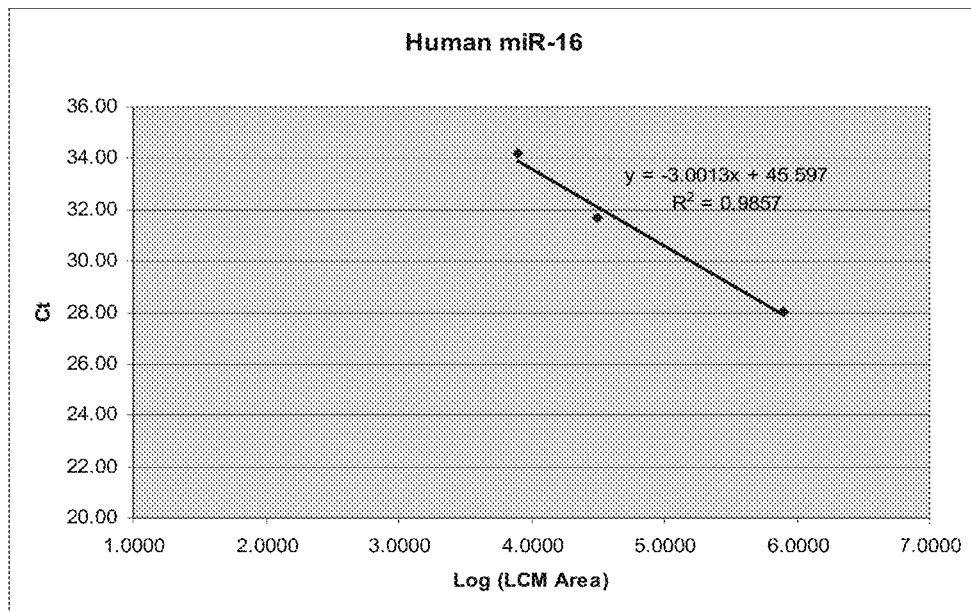
FIG. 10C: miR-16 - miRNA profiling from human bladder LCM samples; LCM area and Ct correlation

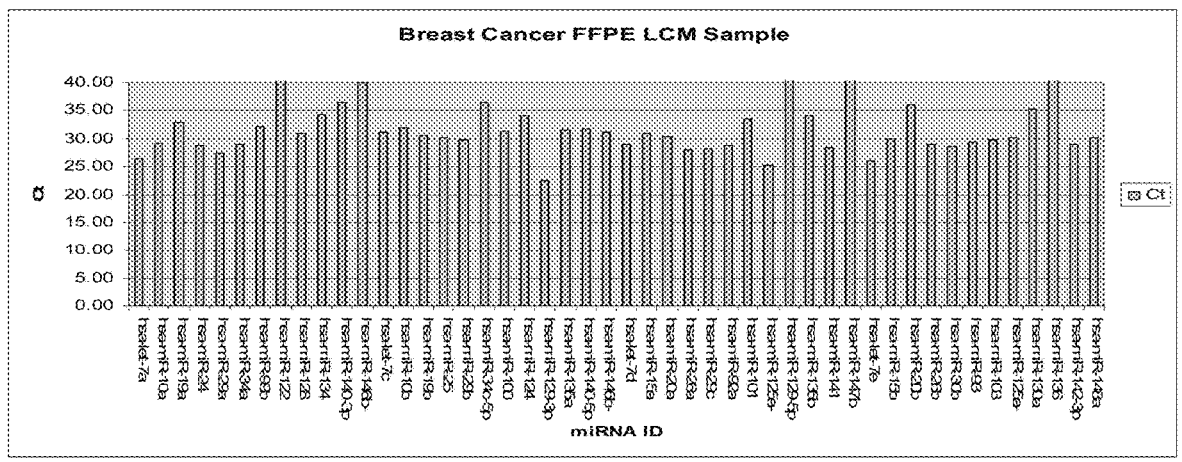
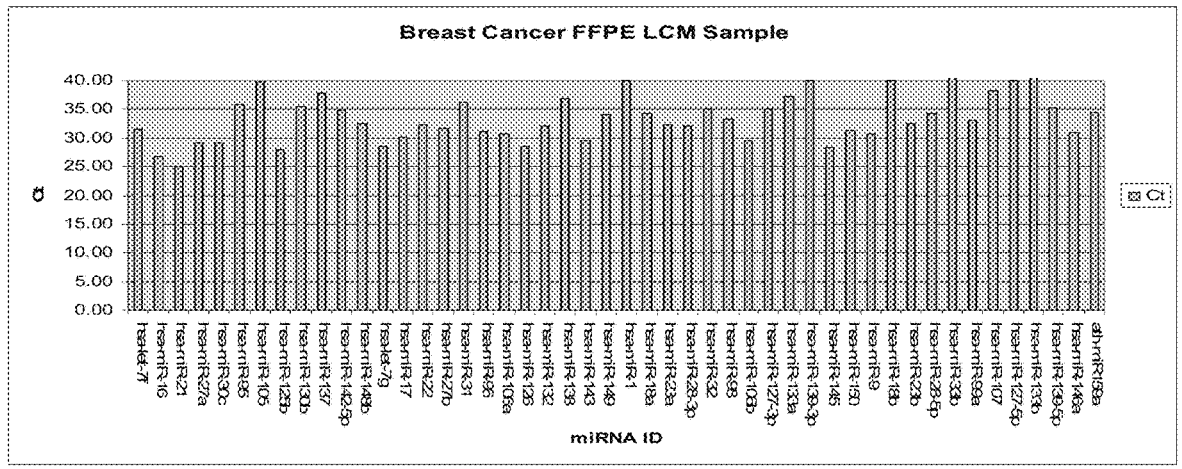
FIG. 11: Breast cancer FFPE sample miRNA profiling

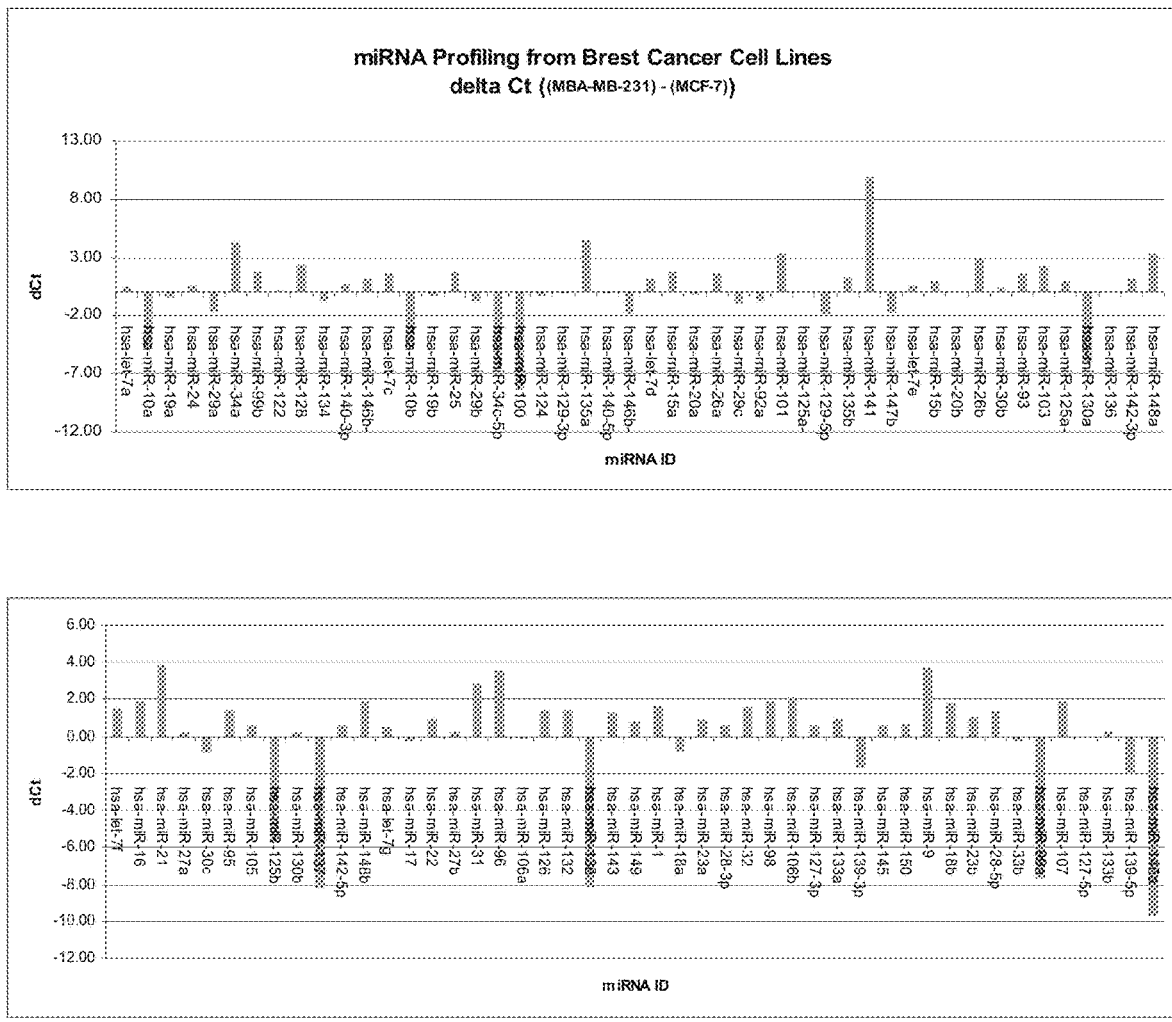
FIG. 12: Difference in expression of miRNA levels between breast cancer lines: MBA-MB-21 minus MCF-7

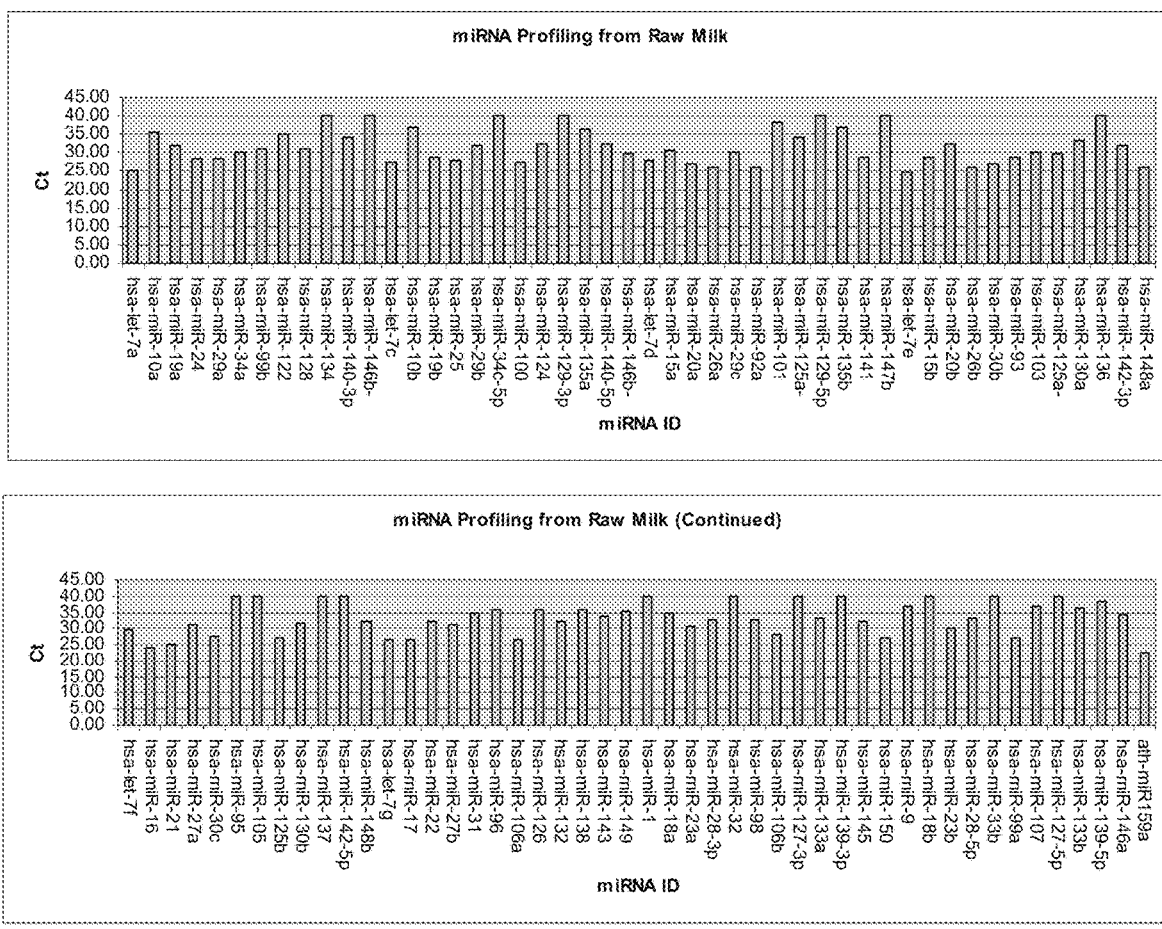
FIG. 13: miRNA profiling from raw cow milk

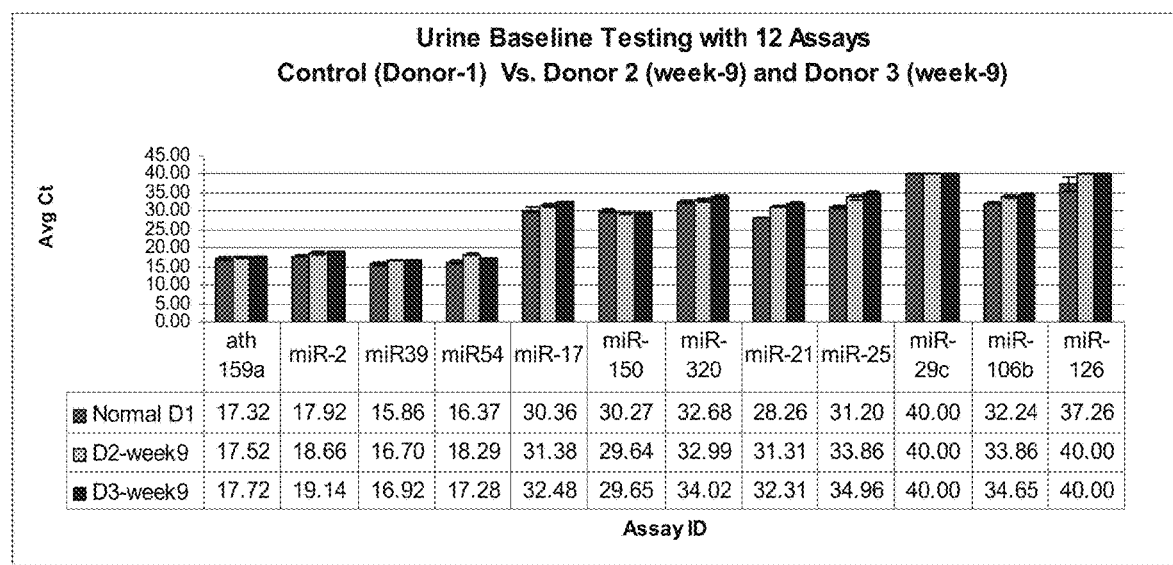
FIG. 14: miRNA profiling from urine

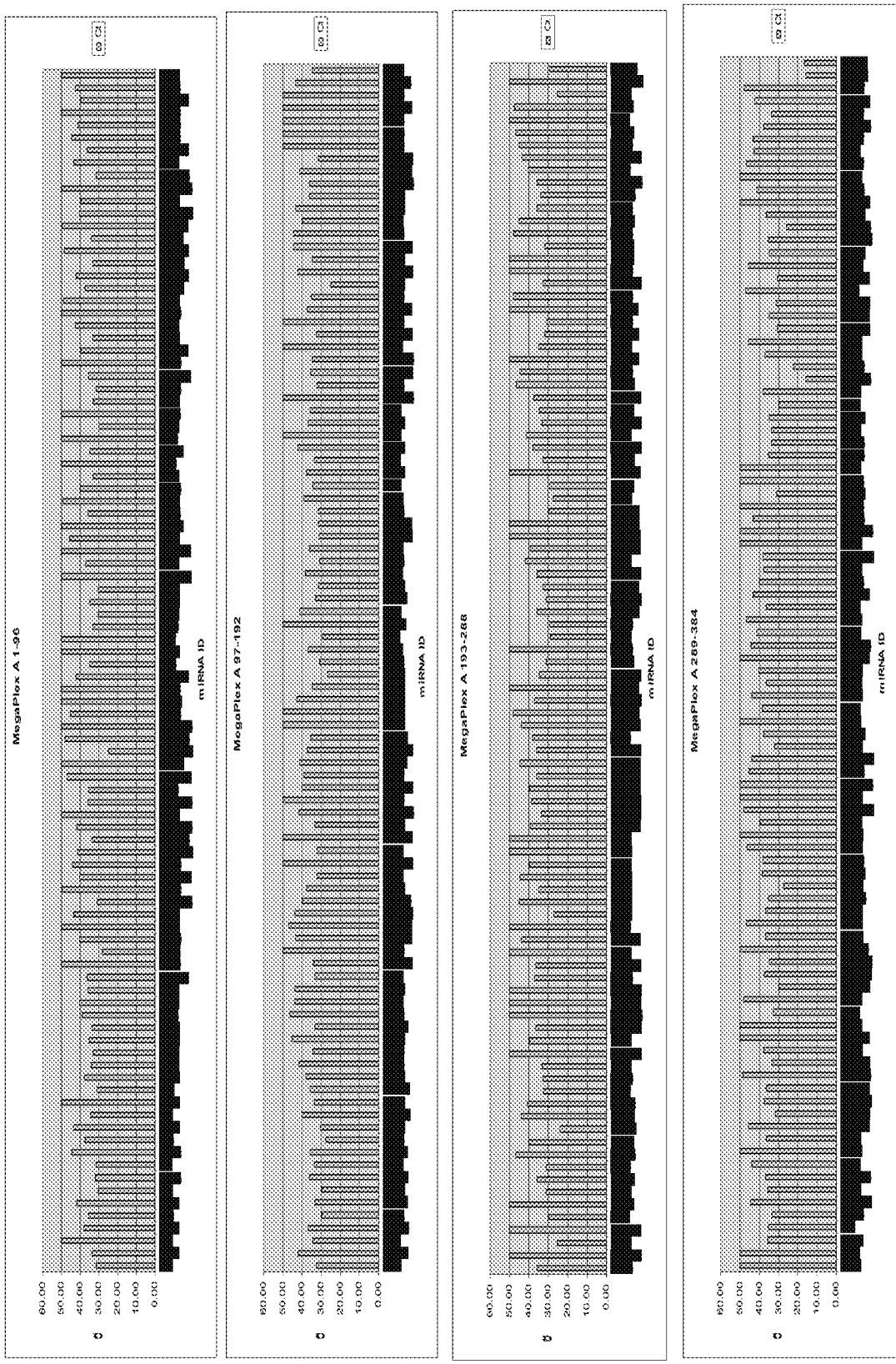
FIG. 15: MegaPlex A miRNA Profiling from 25 microL Serum

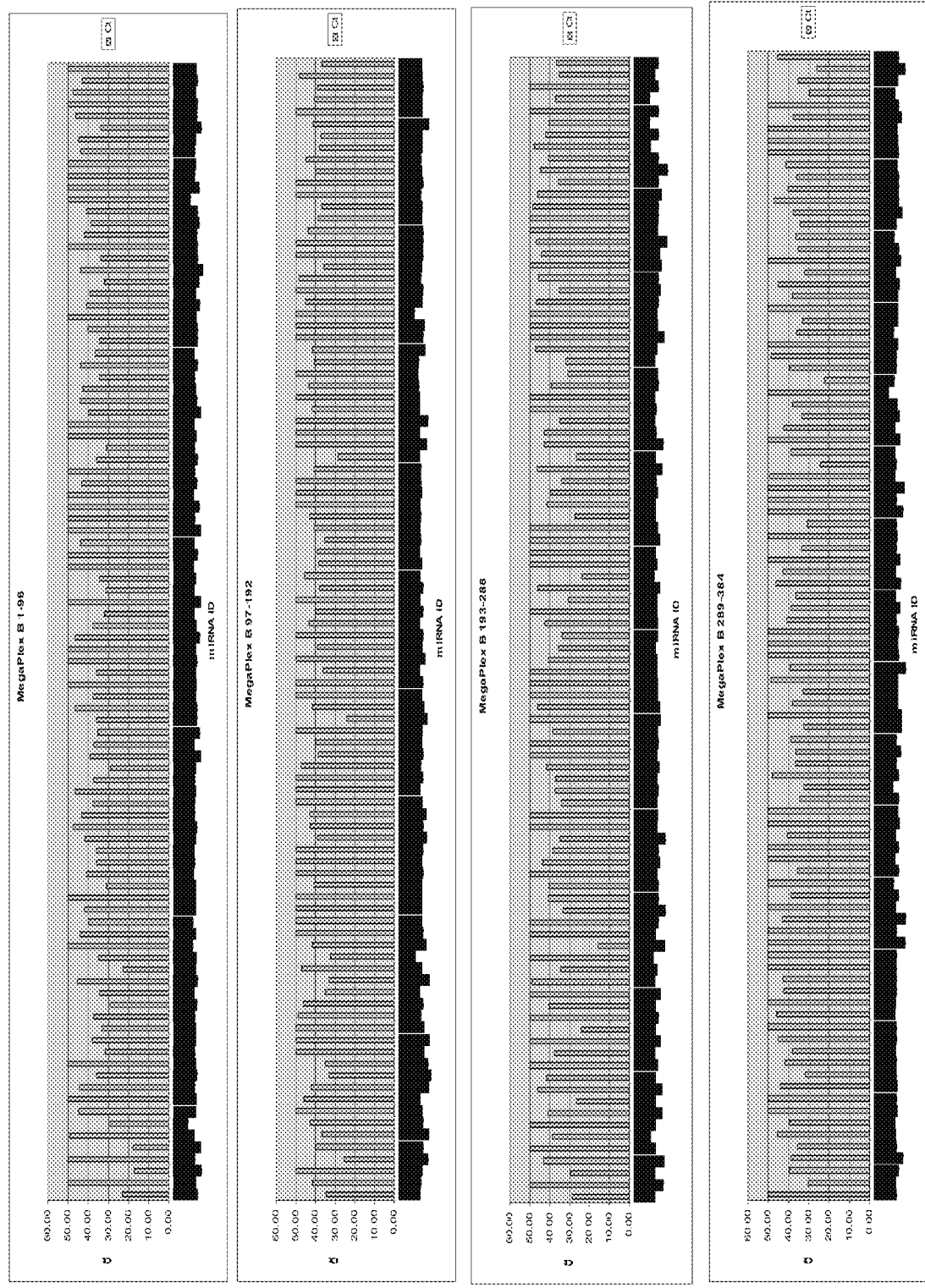
FIG. 16: MegaPlex B miRNA Profiling from 25 microL Serum

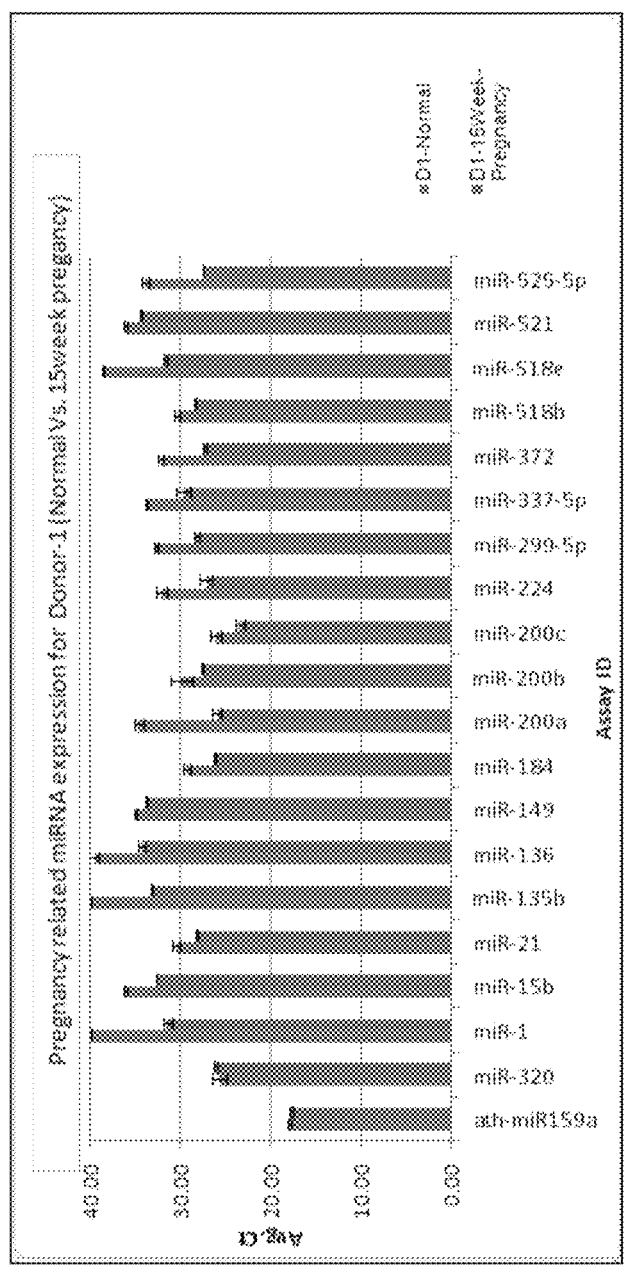
FIG. 17: miRNA expression before and at 15-week of pregnancy.

SEQUENCE LISTING

<160> NUMBER OF SEQ ID NOS: 3

<210> SEQ ID NO 1
<211> LENGTH: 22
<212> TYPE: DNA
<213> ORGANISM: Homo sapiens

<400> SEQUENCE: 1
aactatacaa cctactacct ca                                              22

<210> SEQ ID NO 2
<211> LENGTH: 22
<212> TYPE: DNA
<213> ORGANISM: Homo sapiens

<400> SEQUENCE: 2
aaccacacaa cctactacct ca                                              22

<210> SEQ ID NO 3
<211> LENGTH: 19
<212> TYPE: DNA
<213> ORGANISM: Homo sapiens

<400> SEQUENCE: 3
gcggagggaa gctcatcag                                                  19

METHODS FOR ISOLATION, IDENTIFICATION, AND QUANTIFICATION OF MIRNAS

CROSS REFERENCE TO RELATED APPLICATIONS

This application is a division of U.S. Nonprovisional patent application Ser. No. 13/350,277, filed Jan. 13, 2012, which claims the benefit of priority under 35 U.S.C. § 119(e) to U.S. Provisional Patent Application No. 61/432,874, filed 14 Jan. 2011, which are herein incorporated by reference in their entirety.

FIELD OF THE INVENTION

This application relates to method and compositions and kits for isolation, identification, and quantification of miRNAs and other RNAs, including but not limited to, siRNAs, mRNAs, and snRNAs.

BACKGROUND

MicroRNAs regulate virtually every aspect of biology, including developmental timing, differentiation, proliferation, antiviral defense and metabolism. MicroRNAs are ~22-nucleotide-long RNAs that are generated by sequential processing from longer transcripts that contain a stem-loop. One strand is loaded into the miRNA-induced silencing complex (miRISC), which contains the proteins argonaute (Ago) and Tnrc6 (trinucleotide repeat-containing 6; GW182). The other strand is usually degraded. The mature miRNA guides the miRISC to partially complementary sequences, termed miRNA recognition elements (MREs), in target mRNAs to repress mRNA translation, promote transcript decay or both. MicroRNAs probably regulate the expression of most coding genes. miRNAs have been reported from all living organisms, including humans, bacteria, viruses, plants, worms, and others. About 3% of human genes encode for miRNAs and about 30% of genes are believed to be regulated by miRNAs. It has also been widely reported that an abnormal level of miRNA expression or presence is associated with diseases, such as cancer, heart attack, diabetes, etc.

Quantitative and qualitative isolation of miRNAs from various biological samples has been hampered for several reasons, including, but not limited to, labor-intensive and time consuming protocols; the nature of small size of miRNA leads to easy loss of the targets during extraction; miRNAs, like other RNAs, are not stable and can be degraded easily during processing and storage; the miRNA detection rate from real patient samples is usually low or undetectable, i.e., not quantitative; and further the extracted miRNA targets normally are poorly correlated between related study objects (e.g. placenta vs. blood).

For example, most miRNA (or RNA), isolation reagents or kits that are commercially available (from QIAGEN-PAXGENE blood RNA kit, AMBION-LEUKOLOCK total RNA kit, and others), suffer from one or more of the following drawbacks: low sensitivity and detectability; low yield; not reproducible; large sample volume requirement; miRNA extraction does not scale well; time-consuming workflows, 4-5 hours workflow in general; low throughput and not automatable. Thus, there is a need in the field for better methods for isolating, identifying, and quantifying miRNAs.

BRIEF DESCRIPTION OF THE DRAWINGS

FIG. 1: Schematic for making anti-miRNA probe beads using chemical synthesis. Exemplary sequence shown in figure is AACTATACAACCTACTACCTCA (SEQ ID NO:1).

FIG. 2: Schematic for enzymatic synthesis of anti-miRNA probe beads. Exemplary sequence shown in figure is GCG-GAGGGAAGCTCATCAG (SEQ ID NO:3).

FIG. 3A: Non-anti-probe beads hybridization with Cy3-laneled Let-7a.

FIG. 3B: Anti-Let-7a-probe beads hybridization with Cy3-labeled Let-7a.

FIG. 3C: FACS after de-hybridization of Cy3-labeled Let-7a bond from anti-Let-7a-probe beads.

FIG. 4: Let-7 family miRNA profiling by $C_t$ values.

FIG. 5: miRNA detection after addition (spiking) to plasma.

FIG. 6A: Quantitative real-time PCR Ct profiles of 96 miRNAs from blood.

FIG. 6B: Quantitative real-time PCR Ct profiles of 95 miRNAs from blood.

FIG. 7: Saliva miRNA profiling using anti-miRNA probe beads.

FIG. 8: A384C6 Beads showing Sensitivity and Dynamic Range of anti-miRNA probe beads.

FIG. 9: miRNA Detectability and reproducibility.

FIG. 10A: Let7a-miRNA profiling from human bladder LCM samples; LCM area and Ct correlation.

FIG. 10B: Let7c-miRNA profiling from human bladder LCM samples; LCM area and Ct correlation.

FIG. 10C: miR-16-miRNA profiling from human bladder LCM samples; LCM area and Ct correlation.

FIG. 11: Breast cancer FFPE sample miRNA profiling.

FIG. 12: Difference in expression of miRNA levels between breast cancer lines: MBA-MB-21 versus MCF-7 (delta Ct is shown).

FIG. 13: miRNA profiling from raw cow milk.

FIG. 14: miRNA profiling from urine from three donors.

FIG. 15: Megaplex A miRNA profiling from 25 microL serum.

FIG. 16: Megaplex B miRNA profiling from 25 microL serum.

FIG. 17: miRNA expression before and at 15-week of pregnancy.

SUMMARY OF THE INVENTION

As described above, the isolation, detection and quantification of miRNAs have been a daunting problem. Applicants have now developed a simple and elegant solution to the problem. In one embodiment, the invention relates to a method for isolating, identifying, or quantifying an miRNA from a sample of interest, comprising: contacting the sample of interest with an anti-miRNA probe covalently attached to a bead; incubating the sample of interest—bead mixture under suitable conditions to form hybridized complexes between the miRNA in the sample of interest and the anti-miRNA probes on the beads; washing the beads under suitable conditions to remove the unbound sample material; and isolating, identifying, or quantifying the miRNA bound to the anti-miRNA probes.

In a further embodiment of the invention, the miRNA is isolated from the anti-miRNA probe beads before identifying or quantifying the miRNA.

In another embodiment of the invention, the identifying or quantifying the miRNA is comprises using reverse transcription followed by conventional or real-time or quantitative polymerase chain reaction (q-PCR) or other methods of amplification. In another embodiment, the identifying or quantifying a miRNA involves non-qPCR techniques.

In one embodiment of the invention, the beads are magnetic beads. In another embodiment of the invention, the beads are non-magnetic beads. In one embodiment of the invention, the beads are carboxylic acid functionalized beads. In another embodiment of the invention, the beads are DNA beads. In another embodiment of the invention, the beads are P1 DNA beads.

In one embodiment of the invention, the anti-miRNA probe is attached to the beads using chemical synthesis.

In another embodiment of the invention, the anti-miRNA probe is attached to the beads using enzymatic synthesis. In another embodiment of the invention, the enzymatic synthesis comprises: taking an oligonucleotide that has a sequence complementary to an miRNA of interest (anti-miRNA probe); adding a terminal didexoy nucleotide to the 3' end using a terminal transferase; adding a 5'-phosphate group to the oligonucleotide using a kinase; and ligating the oligonucleotide to DNA beads using a single-strand DNA ligase. In one embodiment, the kinase is a T4 polynucleotide kinase.

In one embodiment of the invention, a single species of ant-miRNA probe is attached to an individual bead. In another embodiment of the invention more than one species of anti-miRNA probes are attached to an individual bead.

In one embodiment of the invention, sample of interest is a biological sample. In another embodiment of the invention, the biological sample is selected from the group consisting of blood, serum, plasma, urine, saliva, cerebrospinal fluid, wound exudates, biopsies, autopsies, tissues, formalin-fixed, paraffin-embedded (FFPE) samples, or organs. In another embodiment of the invention, the biological sample is a biological fluid. In another embodiment of the invention, the biological fluid is blood. In another embodiment of the invention, the biological fluid is plasma. In another embodiment of the invention, the biological fluid is serum. In another embodiment of the invention, the biological fluid is saliva. In another embodiment, the sample could be a fossil or a fossilized rock or sediment.

In another embodiment, a method of diagnosing a disease or disease progression is disclosed, comprising: identifying a set of miRNA markers that are differentially regulated during a causation or progression of a disease; isolating and measuring the levels of such miRNA markers from a suitable biological sample from a patient in need thereof, at different time points if necessary; and diagnosing the disease or its progression over time in the patient.

In another embodiment of the invention, a kit for isolating, identifying, or quantifying an miRNA from a sample of interest is provided, comprising: beads comprising anti-miRNA probe molecules covalently attached thereto; a wash buffer; and an elution buffer.

In another embodiment of the kit an instruction leaflet may be included describing the product and protocol to carry out the inventive method.

DETAILED DESCRIPTION OF THE INVENTION

It is to be understood that the particular methods, reaction mixtures, and/or systems described herein may vary. The terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. As used in this specification and the appended claims, the singular forms "a", "an", and "the" also include plural referents unless the context clearly provides otherwise. All numerical ranges are intended to encompass each individual value within the range as if each were separately listed (e.g., 10-20 may include one or more of 10, 11, 12, 13, 14, 15, 16, 17, 18, 19 and/or 20). In terms of concentration ranges, these encompass fractional ranges, e.g., all values between 10-20, represents as if each were individually written out (e.g., 10.8, 11.5). The term "approximately", when used to modify a group of numerical values, is meant to apply to each value individually unless otherwise indicated.

An "amplicon" typically refers to a molecule made by copying or transcribing another molecule, e.g., as occurs in transcription, cloning, and/or in a polymerase chain reaction ("PCR") (e.g., strand displacement PCR amplification (SDA), duplex PCR amplification, etc.) or other nucleic acid amplification technique. Typically, an amplicon is a copy of a selected nucleic acid or a portion thereof (e.g., a template or target nucleic acid) or is complementary thereto. The term "amplifying" or "amplification" in the context of nucleic acids typically refers to the production of multiple copies of a polynucleotide, or a portion of the polynucleotide, typically starting from a small amount of the polynucleotide (e.g., a single polynucleotide molecule), where the amplification products or amplicons are generally detectable. Any of several methods may be used to amplify the target nucleic acid from the sample. The term "amplifying" which typically refers to an "exponential" increase in target nucleic acid is being used herein to describe both linear and exponential increases in the numbers of a select target sequence of nucleic acid. The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. Exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., WO 2006/081222), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990) and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al. Nat. Genet. 19: 225-232 (1998); and/or Banér al. Nucleic Acid Res., 26: 5073-5078 (1998)), and strand displacement amplification (SDA) (Little, et al. Clin Chem 45:777-784 (1999)), among others. Many systems are suitable for use in amplifying target nucleic acids and are contemplated herein as would be understood by one of skill in the art.

Any of several methods may be used to detect target nucleic acids using various primers and/or probes. Many different reagents, systems, and/or detectable labels may be used in the methods described herein. These include, for example, TaqMan® systems, detectable label-quencher systems (e.g., FRET, salicylate/DTPA ligand systems (see, e.g., Oser et al. Angew. Chem. Int. Engl. 29(10):1167 (1990), displacement hybridization, homologous probes, assays described in EP 070685), molecular beacons (e.g., NASBA), Scorpion, locked nucleic acid (LNA) bases (Singh, et al. Chem Commun 4:455-456 (1998)), peptide nucleic acid (PNA) probes (Pellestor, et al. European J. Human Gen. 12:694-700 (2004)), Eclipse probes (Afonina, et al. Biotechniques 32:940-949 (2002)), light-up probes (Svanvik, et al. Anal Biochem 281:26-35 (2001)), molecular beacons (Tyagi, et al. Nat. Biotechnol. 14:303-308 (1996)), tripartite molecular beacons (Nutiu, et al. Nucleic Acids Res. 30:e94 (2002)), QuantiProbes (www.qiagen.com), HyBeacons (French, et al. Mol. Cell. Probes 15:363-374 (2001)), displacement probes (Li, et al. Nucleic Acids Res. 30:e5 (2002)), HybProbes (Cardullo, et al. PNAS 85:8790-8794 (1988)), MGB Alert (www.nanogen.com), Q-PNA (Fiandaca, et al. Genome Res. 11:609-611 (2001)), Plexor (www.Promega.com), LUX primers (Nazarenko, et al. Nucleic Acids Res. 30:e37 (2002)), Scorpion primers (Whitcombe, et al. Nat Biotechnol 17:804-807 (1999)), AmpliFluor (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress. An apparatus for detecting the signal generated by the detectable label may be used to detect, measure, and quantify the signal before, during, and/or after amplification. The particular type of signal may dictate the choice of detection method. For example, in some embodiments, fluorescent dyes are used to label probes and/or amplified products. The probes bind to single-stranded and/or double-stranded amplified products, and/or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence may be quantitated using standard equipment such as a spectra-fluorometer, for example. The use of other methods and/or reagents is also contemplated herein.

One exemplary method for amplifying and detecting target nucleic acids is commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900). TaqMan® assays are typically carried out by performing nucleic acid amplification on a target polynucleotide using a nucleic acid polymerase having 5'-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system utilizes double-stranded probes in displacement hybridization methods (see, e.g., Morrison et al. Anal. Biochem., 18:231-244 (1989); and/or Li, et al. Nucleic Acids Res., 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for amplifying and detecting target nucleic acids involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher dye that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for amplifying RNA to double stranded DNA without temperature cycling. A NASBA reaction typically requires avian myeloblastosis virus reverse transcriptase (AMV-RT or AMV), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpion system is another exemplary assay format that may be used in the methods described herein. Scorpion primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., HEG monomer) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpion system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for molecular beacons are known in the art and would be suitable for use in the methods described herein.

One or more detectable labels and/or quenching agents are typically attached to an oligonucleotide primer and/or probe. The detectable label may emit a signal when free or when bound to the target nucleic acid. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorophore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluorosceins (e.g., 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC, WT), Texas Red, Texas Red-X, VIC and other labels described in, e.g., US Pub. No. 2009/0197254), among others as would be known to those of skill in the art. Other detectable labels may also be used (see, e.g., US Pub. No. 2009/0197254), as would be known to those of skill in the art.

Nucleic acid binding agents may also be used to detect nucleic acids amplified using the methods described herein. Many suitable detectable nucleic acid binding agents are available to one of skill in the art and may be used alone or in combination with other agents and/or components of an assay system. Exemplary DNA binding agents may include, for example, acridines (e.g., acridine orange, acriflavine), actinomycin D (Jain, et al. J. Mol. Biol. 68:21 (1972)), anthramycin, BOBO™-1, BOBO™-3, BO-PRO™-1, cbromomycin, DAPI (Kapuseinski, et al. Nuc. Acids Res. 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, 1990, Nuc. Acids Res. 18:3753-3762), Hoechst 33342, homidium, JO-PRO™-1, LIZ dyes, LO-PRO™-1, mepacrine, mithramycin, NED dyes, netropsin, 4'6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX blue, SYTOX green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO™-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reaction by amplifying the target sequence in the presence of the dye, exciting the biological sample with light at a wavelength absorbed by the dye and detecting the emission therefrom; and, determining a melting profile of the amplified target sequence. The presence of amplified products and, therefore, the target sequence in the sample, may thereafter be determined by, for example, performing a melting curve analysis (e.g., non-linear least squares regression of the sum of multiple gaussians). It is to be understood that the use of the SYBR® Green dye is presented as an example and that many such dyes may be used in the methods described herein. Other nucleic acid binding agents may also be suitable as would be understood by one of skill in the art.

Nucleic acids "hybridize" or "anneal" in a base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotides is typically base specific, e.g., A/T and G/C, by Watson/Crick and/or Hoogsteen-type interactions. It is not a requirement that two polynucleotides have 100% complementarity over their full length to achieve hybridization. In some aspects, a hybridization complex can form from intermolecular interactions, or alternatively, can form from intramolecular interactions. Hybridization occurs due to a variety of well-characterized forces, including hydrogen bonding, solvent exclusion, and base stacking. An extensive guide to nucleic hybridization may be found in, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

A "mixture" refers to a combination of two or more different components. A "reaction mixture" refers a mixture that comprises molecules that can participate in and/or facilitate a given reaction or assay. To illustrate, an amplification reaction mixture generally includes a solution containing reagents necessary to carry out an amplification reaction, and typically contains primers, a biocatalyst (e.g., a nucleic acid polymerase, a ligase, etc.), dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components, which includes the biomolecules of the invention.

A "moiety" or "group" refers to one of the portions into which something, such as a molecule, is or can be divided (e.g., a functional group, substituent group, or the like). For example, an oligonucleotide described herein includes at least one donor moiety and/or at least one acceptor moiety in certain embodiments.

The term "mutation" refers to a nucleic acid that has been altered in its nucleic acid sequence or an encoded protein product of a nucleic acid that has been altered in its amino acid sequence relative to an unaltered or native form of the nucleic acid or encoded protein product. Such alterations include, for example, point mutations or substitutions, deletions and insertions.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), locked nucleic acids (LNA™), and the like. In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, a primer, etc. A nucleic acid may be, e.g., single-stranded, double-stranded, triple-stranded (and the like) and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) Chem. Soc. Rev. pp 169-176, which is incorporated by reference). To further illustrate, although a nucleic acid will generally contain phosphodiester bonds, in some cases nucleic acid analogs are included that have alternate backbones. These may include, without limitation, phosphoramide (Beaucage et al. (1993) Tetrahedron 49(10): 1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Brill et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365: 566; and Carlsson et al. (1996) Nature 380:207). Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which are each incorporated by reference. Several nucleic acid analogs are also described in, e.g., Rawls, C & E News Jun. 2, 1997 page 35. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. For instance, certain bases used in nucleotides that act as melting temperature ($T_m$) modifiers are optionally included. Exemplary of these are 7-deazapurines (e.g., 7-deazaguanine, 7-deazaadenine, and the like); pyrazolo[3,4-d]pyrimidines, propynyl-dN (e.g., propynyl-dU, propynyl-dC, and the like); hypoxanthine; inosine; xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil; non-naturally occurring bases as described by, for example, Seela et al. ((1991) Hely. Chim. Acta 74:1790; (1999) Hely. Chim. Acta 82:1640); Grein et al. ((1994) Bioorg. Med. Chem. Lett.

4:971-976), U.S. Pat. Nos. 5,484,908, 5,645,985, 5,990,303, 5,830,653, 6,639,059, 6,303,315, U.S. Pat. Appln. No. 2003/0092905, and the like.

"Nucleoside" typically refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, and the like. A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside. Nucleoside triphosphates and 2'-deoxynucleoside triphosphates or their chemically modified versions may be used as substrates for multiple-nucleotide extension by APP where, for example, one nucleotide is incorporated the extending strand can be further extended. 2',3'-dideoxynucleoside triphosphates, chemically modified versions thereof, or other suitable compounds (e.g., as in US 2005/0037398A1, acycloNMP) may be used as terminators for further extension may be used for single-nucleotide extension. 2',3'-dideoxynucleoside triphosphates may be labeled with radioactivity or fluorescence dye for differentiation from the 3' terminal dideoxynucleotide of oligonucleotide P*. Mixtures of nucleoside triphosphates or 2'-deoxynucleoside triphosphates and 2', 3'-dideoxynucleoside triphosphates may also be used.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases (e.g., RQY polymerase described above), telomerases, polynucleotide phosphorylases, and the like. A "thermostable enzyme" refers to an enzyme that is stable to heat, is heat resistant, and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known to persons skilled in the art and are exemplified in, for example, U.S. Pat. Nos. 4,683,202, 4,683,195, and 4,965,188. To further illustrate, a "thermostable polymerase" refers to an enzyme that is suitable for use in a temperature cycling reaction, such as a polymerase chain reaction ("PCR"). For a thermostable polymerase, enzymatic activity refers to the catalysis of the combination of the nucleotides in the proper manner to form primer extension products that are complementary to a template nucleic acid. Exemplary thermostable polymerases are described herein, and others may available to the skilled artisan may also be suitable.

TdT terminal deoxynucleotidyl transferase) catalyses the addition of nucleotides to the 3' terminus of a DNA molecule. Unlike most DNA polymerases it does not require a template. The preferred substrate of this enzyme is a 3'-overhang, but it can also add nucleotides to blunt or recessed 3' ends. Cobalt is a necessary cofactor, however the enzyme catalyzes reaction upon Mg and Mn administration in vitro.

CircLigase™ (Epicentre Biotechnologies), ssDNA Ligase is a thermostable ATP-dependent ligase that catalyzes intramolecular ligation (i.e. circularization) of ssDNA templates having a 5'-phosphate and a 3'-hydroxyl group. In contrast to T4 DNA Ligase and Ampligase® DNA Ligase, which ligate DNA ends that are annealed adjacent to each other on a complementary DNA sequence, CircLigase ssDNA Ligase ligates ends of ssDNA in the absence of a complementary sequence. The enzyme is therefore useful for making circular ssDNA molecules from linear ssDNA. Circular ssDNA molecules can be used as substrates for rolling-circle replication or rolling-circle transcription. Linear ssDNA of >30 bases is circularized by CircLigase enzyme. Under standard reaction conditions, virtually no linear concatamers or circular concatamers are produced. In addition to its activity on ssDNA, CircLigase enzyme also has activity in ligating a single-stranded nucleic acid having a 3'-hydroxyl ribonucleotide and a 5'-phosphorylated ribonucleotide or deoxyribonucleotide.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na_+$, and the like, if such counterions are present. Typically, the 3' end linkage of P* is a phosphodiester bond. Oligonucleotides may be prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. ((1979) Meth. Enzymol. 68:90-99); the phosphodiester method of Brown et al. ((1979) Meth. Enzymol. 68:109-151); the diethylphosphoramidite method of Beaucage et al. ((1981) Tetrahedron Lett. 22:1859-1862); the triester method of Matteucci et al. ((1981) J. Am. Chem. Soc. 103:3185-3191); automated synthesis methods; or the solid support method described in U.S. Pat. No. 4,458,066, and/or other methods known to those skilled in the art.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide). Although other primer nucleic acid lengths are optionally utilized, they typically comprise hybridizing regions that range from about 8 to about 100 nucleotides in length. Shorter primer nucleic acids generally require lower temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid may be labeled, if desired, by incorporating a detectable label as described herein.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under selected hybridization conditions. A hybridization assay carried out using a probe under sufficiently stringent hybridization conditions permits the selective detection of a specific target sequence. The term "hybridizing region" refers to that region of a nucleic acid that is exactly or substantially complementary to, and therefore capable of hybridizing to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support. A probe of the invention may be generally included in a nucleic acid that comprises one or more labels (e.g., donor moieties, acceptor moieties, and/or quencher moieties), such as a 5'-nuclease probe, a hybridization probe, a fluorescent resonance energy transfer (FRET) probe, a hairpin probe, or a molecular beacon, which can also be utilized to detect hybridization between the probe and target nucleic acids in a sample. In some embodiments, the hybridizing region of the probe is completely complementary to the target sequence. However, in general, complete complementarity is not necessary (e.g., nucleic acids can be partially complementary to one another); stable hybridization complexes may contain mismatched bases or unmatched bases. Modification of the stringent conditions may be necessary to permit a stable hybridization complex with one or more base pair mismatches or unmatched bases. Sambrook et al., Molecular Cloning: A Laboratory Manual, 3rd Ed., Cold Spring Harbor Laboratory Press, Cold Spring Harbor, N.Y. (2001) provides guidance for suitable modification. Stability of the target/probe hybridization complex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

The methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, or spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods may be useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. The kit typically includes at least a pair of oligonucleotides (e.g., at least one of the pair being a P* oligonucleotide) for amplifying at least one target nucleic acid from a sample, one or more polyphosphorolyzing agents described herein, a biocatalyst (e.g., DNA polymerase) and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. Other embodiments of particular systems and kits are also contemplated.

Magnetic polymer particles are of general utility in various medical and biochemical fields, for example as transport vehicles for the delivery of pharmaceutical products, for diagnostic purposes, for separation and for synthetic purposes. Such particles rely upon their magnetic properties in order to perform these functions: in diagnostic assay applications, for example, application of a magnetic field to a sample containing an analyte bound to magnetic polymer particles allows the isolation of the analyte without the use of centrifugation or filtration; and in therapeutic applications, for example, application of a magnetic field to the patient may serve to target drug-carrying magnetic polymer particles to a desired body site.

By magnetic is meant herein that the polymer particles contain superparamagnetic crystals. Thus the magnetic polymer particles are magnetically displaceable but are not permanently magnetizable. Many processes for preparing magnetic polymer particles are known, a large number of which involve preparing maghemite- or magnetite-containing polymer particles from pre-formed magnetic iron oxides, e.g. magnetite. Some of processes involved are described in U.S. Pat. No. 4,654,267 (Ugelstad).

The magnetic polymer particles used in the process of the invention may be any magnetic polymer particle e.g. as described in U.S. Pat. No. 4,654,267. The particles are preferably porous to allow the presence of the superparamagnetic crystals in the pores thereof. The surface of the magnetic particles is normally functionalized to allow coupling of a ligand to the polymer particle, e.g. it may be functionalized to carry any known surface structure such as carboxyl groups, tosyl groups, amino groups, epoxy groups, maleamido groups, thiol groups etc. Hence, the surface may be amine functionalized. Alternatively, an amine functionalized surface can itself be further functionalized to carry other functional groups, e.g. COOH groups.

The polymer particle is preferably made from combinations of vinylic polymers (e.g. styrene), acrylates and/or methacrylates. The polymeric material may optionally be cross-linked, for example by incorporation of cross-linking agents, for example as comonomers, e.g. divinylbenzene (DVB) or ethyleneglycol dimethacrylate. Appropriate quantities of the cross-linking agents (e.g. comonomers) required will be well known to the skilled person. Preferably the polymer is a cross-linked styrenic polymer (e.g. a styrene-divinylbenzene polymer, surface functionalized by the use of a nitro-group containing comonomer, e.g. nitro-styrene, and subsequent reduction) or a cross-linked (meth)acrylic polymer surface functionalized by the use of an epoxy-group containing co-monomer (e.g. glycidylmethacrylate) and subsequent amination (e.g. by reaction with ethylene diamine).

The superparamagnetic crystals in the polymer particles used in the process of the invention may be of any material capable of being deposited in superparamagnetic crystalline form in the porous polymer particles. Magnetic iron oxides, e.g. magnetite or maghemite are preferred; however the crystals may be of mixed metal oxides or other magnetic material if desired. The total quantity of crystalline magnetic material present is generally more than 1%, preferably more than 3%, desirably more than or equal to 5% (by weight, e.g. up to 40% wt. The percentage is calculated on a Fe (or equivalent metal in the case of magnetic materials other than iron oxides) weight basis based upon the overall dry weight of the coated particles.

Polymer particles according to the various aspects of the present invention may generally have sizes (i.e. diameters) that are in the micrometer range, e.g. 0.3 to 100 µm, especially 0.5 to 50 µm, more especially 0.8 to 8 µm, e.g. 0.8 to 1.2 µm. 1 µm beads are referred.

Typically the porous particles used will have a surface area of at least 15 m$^2$/g (measured by the BET nitrogen absorption method), and more preferably at least 30 m$^2$/g, e.g. up to 700 m$^2$/g, when corrected to a mean particle diameter of 2.7 µm (i.e. multiply surface area by 2.7/MD, where MD is the mean diameter in micrometers). Similarly scaled, the particle pore volume is preferably at least 0.1 mL/g.

Typically, the polymer particles are spherical and substantially monodisperse before they are coated and especially preferably remain spherical and substantially monodisperse once they have been coated.

By substantially monodisperse, it is meant that for a majority of particles, the particles have a coefficient of variation (CV) of less than 20%, for example less than 15%, preferably less than 12%, more preferably less than 11%, still more preferably less than 10% and most preferably no more than about 8%, e.g. 2 to 5%. CV is determined in percentage as $$CV=(100 \times standard\ deviation)/mean$$

where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV may be performable on a Coulter or other particle size analyzer.

Functionalization of the polymeric material may take place after polymerization by, for example, nitration and subsequent reduction of the thus-formed nitro groups to pendant amine groups; or direct amination, for example by treatment with amino ethanol. As further alternatives, polymeric particles prepared by the well-known Ugelstad two-step swelling process and the improvements thereto disclosed in WO 00/61647 may be used. Porous polymer particles produced according to the processes described in this publication may have magnetic particles deposited in their pores by standard techniques.

As a further possibility, porous polymer particles may be prepared from nitro styrene and DVB, and magnetic material introduced as taught in U.S. Pat. No. 4,654,267.

The superparamagnetic polymer beads sold by Life Technologies (Invitrogen Dynal Biotech ASA), under the trade names DYNABEADS, especially DYNABEADS MYONE are especially preferred. DYNABEADS are particularly advantageous since they remain in suspension and do not exhibit magnetic particle sedimentation often associated with other magnetic beads. DYNABEADS also show excellent magnetic mobility compared to other magnetic particles in which high levels of iron are present. DYNABEADS exhibit beneficial kinetics allowing shorter reaction times and higher throughputs. Their non-specific binding is lower than other magnetic beads and their proper use results in a concentration of the desired material taking place resulting in easier and more efficient washing procedures. DYNABEADS MYONE beads are easy to automate and are monodisperse. DYNABEADS MYONE carboxylic acid beads are used generally; however, other functional groups may also be utilized.

Certain embodiments are further described in the following examples. These embodiments are provided as examples only and are not intended to limit the scope of the claims in any way. All references, including US patents, patent applications, PCT applications and articles cited within this application are incorporated by reference in their entirety into this application.

EXAMPLES

Example 1

Covalent Bead—anti-miRNA Probe bead—Chemical Preparation.

Schematic is shown in FIG. 1.

Reagents: EDC, miRNA oligo, and MYONE beads (Beads: 1 mL=10 mg=10 billion).

One ml of MYONE carboxylic acid beads (10 billion beads) are placed in 1.5 ml microfuge tube. Beads are washed with 1000 µL 10 mM NaOH 3 times. Beads are further washed with 10000 µL deionized H$_2$O, 4 times. pH is adjusted to about 6.5-7. A reaction master mix is prepared in 1.5 mL tube, as follows:
add H$_2$O 80 µL
add 20 µL 5M NaCl
add 248 µL DMSO 1M EDC is prepared in 5 mM aqueous Imidazole-HCl. One mg/5.2 µL=18 mg/100 µL 5 mM aqueous Imidazole is prepared. 192 µL (2×) of 0.5 mM aqueous anti-miRNA oligo is added to the master mix. Beads are suspended in reaction master mix and treated as follows:
remove the H$_2$O from the beads
add 100 µL 1M EDC solution to the reaction master Mix
add the anti-miRNA oligo/Master Mix/EDC to the beads
immediately vortex and sonicate 3 times.
place the tube on a rotator.

The tube is rotated overnight at room temperature. The beads are further washed as follows: Wash with 1000 µL DMSO. Wash 2 times with 1000 µL deionized water. Wash 2 times with 1000 µL 1×TEX (Tris, EDTA, Triton X-100).

Wash 3 times with 1000 μL 1×TEX and heat for 8 min at 80° C. Beads are stored in 1.00 mL 1×TEX at 4° C.

Example 2

Covalent anti-miRNA Bead—Enzymatic Preparation
Schematic is shown in FIG. 2.
3'-Modification and 5'-Phosphorylation of anti-miRNA Probes
Reagents: Terminal Transferase, ddTTP (TriLink),

| miRNA-Probe | Sequence | Tm |
|---|---|---|
| Let-7aP | 5'AACTATACAACCTACTACCTCA (SEQ ID NO: 1) | 46.41 |
| Let-7bP | 5'AACCACACAACCTACTACCTCA (SEQ ID NO: 2) | 54.8 |

3'-Modification Procedure

| Component | Let-7aP | Let-7bP | Final Concentration |
|---|---|---|---|
| 10X Terminal Transferase Buffer | 10 | 10 | 1X |
| 10X Cobalt Chloride | 10 | 10 | 1X |
| 20 U/μL Terminal Transferase | 10 | 10 | 0.4 U/μL |
| 1 mM ddTTP | 10 | 10 | 100 μM |
| 5'P-Probe | 30 | 30 | ~20 uM |
| H₂O | 30 | 30 | |
| Total | 100 | 100 | |
| Input | 19.3OD × | 15.5OD × | |
| Yield Output | 30 μL | 30 μL | |

The reaction is incubated at 37C.° for 2 hrs. The terminal transferase is inactivated by heating the reaction mix at 95° C. for 5 min.

Phosphorylation Procedure

| Component | Let-7aPddT | Let-7bPddT |
|---|---|---|
| Carryover from above | 100 | 100 |
| 10X Kinase Buffer | 20 | 20 |
| 10 mM ATP | 20 | 20 |
| 10 U/μL T4 Kinase | 15 | 15 |
| DI Water | 45 | 45 |
| Total (μL) | 200 | 200 |
| Oligo Output (OD) | F3 1.5 × 50 μL | F3 2.7 × 50 μL |
| | F4 25.9 × 50 μL | F4 26.9 × 50 μL |

The reaction mix is incubated at 37° C. for 1 hr. Purification is done using PD-10 column by desalting.

Bead Ligation with 5P-Let-7a, b, c, d, e and f Probe-3'ddT

Reagents: SOLID™ P1 DNA Beads (ABI), 5P-Let-7a, b, c, d, e and f Probes, Ligation Buffer (EpiCentre Biotechnologies), Ligase (EpiCentre Biotechnologies), ATP (Ambion), MnCl₂ (Teknova), PEG6000 (Emerald Biosystems).

| Component | Stock Concentration | Volume for 2X (μL) | Final Concentration (1X) |
|---|---|---|---|
| 10X Ligation Buffer | 10X | 160 | 1X |
| 50% PEG6000 | 50% | 240 | 7.5% |
| 25 mM MnCl₂ | 25 mM | 160 | 2.5 mM |
| 250 μM ATP | 250 uM | 160 | 25 μM |
| H2O | | 80 | |
| Total | | 800 | |

Pre-Treatment of Beads

Transferred 300 μL beads (10 million/μL×50=500 million beads×6) to a Lo-Bind tube. Placed the Lo-Bind tube in a magnetic rack for 1 min and removed the supernatant. Added 200 μL 1×TEX (Tris-EDTA-Triton X-100) buffer. Sonicated the beads using Covaris Covalent Declump 1. Placed the Lo-Bind tube in a magnetic rack for 1 min and remove the supernatant. Added 150 μL the Buffer mix and 150 μL H₂O. Vortexed. Divided the beads into 6 tubes, 504 μL each. Placed the Lo-Bind tubes in a magnetic rack for 1 min and removed the supernatant.

Added following reaction mix into the tube: Ligation Reaction

| Component | 7a | 7b | 7c | 7d | 7e | 7f |
|---|---|---|---|---|---|---|
| Solid P1 Beads (500 million beads) | 500 million | 500 million | 500 million | 500 million | 500 million | 500 million |
| 2X Buffer Mix | 100 | 100 | 100 | 100 | 100 | 100 |
| 5'P-Let-7P-3'-ddT A260 | 11.8 A260 | 10.5 A260 | 4.92 A260 | 4.44 A260 | 4.59 A260 | 4.55 A260 |
| 5'P-Let-7P-3'-ddT | 40 | 40 | 80 | 80 | 80 | 80 |
| H₂O | 40 | 40 | 0 | 0 | 0 | 0 |
| 100 U/μL CircLigase I | 20 | 20 | 20 | 20 | 20 | 20 |
| Total | 200 | 200 | 200 | 200 | 200 | 200 |

Incubated reaction tubes at 60° C. overnight on Thermo-Mixer at 1100 rpm.

Bead Clean-up:

Denaturing Solution: Added 200 μL Denaturant to 1800 μL, 1× Denaturing buffer and mixed well. Placed the reaction tube in a magnetic rack for 1 min and remove the supernatant. Added 200 μL 1×TEX buffer. Sonicated the beads using Covaris Covalent Declump 1. Placed the tube in a magnetic rack for 1 min and removed the supernatant. Added 200 μL of the Denaturing Buffer, vortexed, and let stand for 1 min. Placed the tube in a magnetic rack for 1 min and removed the supernatant. Added 200 μL 1×TEX buffer, vortexed and pulsed down. Placed the tube in a magnetic rack for 1 min and removed the supernatant. Repeat twice. Beads are stored (in 200 μL TEX buffer, ~2.5 million beads/μL) at 4° C.

Example 3

Hybridization of Ant-miRNA Beads (Hybridization with Cy3-Labeled miRNA)

Fluorescent flow cytometry analysis is done to ensure that anti-miRNA probes are covalently attached to the beads and that Cy3-labeled miRNAs are effectively captured by the anti-miRNA beads.

Reagents: Anti-ath-miR159 Beads, Cy-3-ath-miR159a, Control: non-anti-probe beads, Cy3-ath-miR159a.

Hybridization is carried out using the following protocol:

Sonicate the beads with Covalent Declump 1 on Covaris. Aliquot 1 μL of ath-miR159a beads and 1 μL Solid P1 beads into 1.5 mL LoBind tubes separately. Add 100 μL hybridization buffer. Add 5 μL 100 μM Cy3-ath-miR159a and vortex. Shake tubes at 1200 rpm for 20 min at room temperature. Magnet the beads for 1 mins and remove the supernatant. Add 200 μL RNA Purification Wash Solution 1 (ABI). Vortex and incubate for 1 min before placing tubes on magnetic rack. Magnet and after 1 min, remove the supernatant. Add 200 μL RNA Purification Wash Solution 2 (ABI). Vortex and incubate for 1 min before placing tubes on magnetic rack. Add 200 μL 0.5×SSPE/T buffer (ABI). Vortex and incubate for 1 min before placing tubes on magnetic rack. Briefly spin the tubes, magnet, and after 1 min, remove the supernatant. Add 100 μL 0.5×SSPE/T Buffer, vortex, and sonicate with an ultrasonic bath briefly. ABI is Applied BioSystems, Inc. miRNAs may be eluted from the beads by de-hybridization using buffers that are known to one skilled in the art, e.g., 10 mM Tris:HCl or 10 mM Tris:HCl with 01 mM EDTA.

Fluorescent Flow Cytometry (FACS) (BD Bioscience) Analysis

Add about 2504 FACS read buffer. Add 10 μL beads. Read. The beads are fluorescent and the center of the distribution peak of the beads is distinctively different from the control beads. Representative FACS profiles are shown in FIGS. 3A-3C.

Example 4

Let-7 miRNA Profiling from Red Blood Cells and Plasma

Reagents: P1-Let-7a-f Beads, Tempus Buffer (ABI), Finger Tip Fresh Blood

Blood Sample Collection: 40 μL of fresh finger blood sample was collected in a tube containing 0.4 μL of 0.5M EDTA (pH 8.0) using a mini finger lancet.

Plasma and Red Blood Cells Separation and Lysis: The blood sample is centrifuged and the plasma is carefully pipetted out. 20 μL plasma is mixed with 40 μL Tempus buffer. The red blood cells are washed with 100 μL 0.9% NaCl, centrifuged, and the supernatant is removed. Washing is repeated 2 more times. 10 μL red blood cells are mixed with 20 μL Tempus Buffer.

Hyb Sample Serial Dilution: 6 μL of the lysate solution prepared above is diluted in 19 μL Oligo dT hybridization buffer and vortexed. This is Hyb sample A (1 μL blood in 100 μL volume). The samples are serially diluted according to following table for the rest of Hyb samples.

| Hyb Sample | Oligo dT Lys/ Bind Buffer | Sample and Volume | Total Volume, μL | Blood, nL |
|---|---|---|---|---|
| A |  |  |  | 1000 |
| B | 135 | A: 15 μL | 150 | 100 |
| C | 135 | B: 15 μL | 150 | 10 |
| D | 135 | C: 15 μL | 150 | 1 |
| E | 135 | D: 15 μL | 150 | 0.1 |

Hybridization: 5 μL each of Let-7a thru Let-7f beads (~2.5 million/μL, 12.5 million total each) are combined in a LoBind tube, 200 μL TEX buffer is added, and the tubes are vortexed. Tubes/beads are magnetized to remove the supernatant. 6 μL of the mixed beads are added into each hybridization sample as prepared above. The beads are shaken at 1100 rpm for 20 min at room temperature. The beads are magnetized to remove the supernatants. The beads are washed according to the following table. Finally, 1×TE buffer is added and the beads are sonicated with Covalent Declump 1.

| Test | Beads | Wash 1, 100 μL | Wash 2, 100 μL | Suspension, 100 μL 1X TE |
|---|---|---|---|---|
| A | Let-7a-f | Buffer A | Buffer B | 1X TE (0.125 million/μL) |
| B | Let-7a-f | Buffer A | Buffer B | 1X TE (0.125 million/μL) |
| C | Let-7a-f | Buffer A | Buffer B | 1X TE (0.125 million/μL) |
| D | Let-7a-f | Buffer A | Buffer B | 1X TE (0.125 million/μL) |
| E | Let-7a-f | Buffer A | Buffer B | 1X TE (0.125 million/μL) |

Reverse Transcription (RT): The captured miRNAs (in suspension, above Table) are reverse transcribed to cDNA using TaqMan® MicroRNA Reverse Transcription Kit (ABI) following the recommended protocol. The reactions are incubated at 16° C./30 min, 42° C./30 min, and 85° C./5 min.

TaqMan PCR Reaction: The reverse-transcribed cDNA from the captured miRNAs are quantitatively analyzed using Applied Biosystems miRNA TaqMan assays and TaqMan Universal PCR Master Mix following the recommended protocols. TaqMan real-time PCR reactions are run on Applied Biosystems 7500 instrument using the default cycling parameters. The results are listed in Table 1 and FIG. 4.

TABLE 1

($C_t$ values for each Let-7 species are shown)

| Blood Volume | Let-7a | Let-7b | Let-7c | Let-7d | Let-7e | Let-7f |
|---|---|---|---|---|---|---|
| NTC | 40.00 | 40.00 | 40.00 | 40.00 | 40.00 | 39.00 |
| 1 nL | 33.21 | 32.89 | 34.48 | 36.17 | 39.03 | 34.34 |
| 10 nL | 31.01 | 30.99 | 36.54 | 32.01 | 36.08 | 34.33 |
| 100 nL | 27.74 | 27.68 | 34.12 | 28.24 | 37.28 | 30.27 |
| 1000 nL | 24.25 | 24.52 | 31.46 | 25.19 | 35.32 | 27.92 |
| 10000 nL | 21.78 | 21.03 | 27.50 | 22.46 | 32.57 | 24.19 |
| Linear Data Points | 4 | 4 | 3 | 5 | 2 | 4 |
| Slope | 3.12 | 3.30 | 3.31 | 3.42 |  | 3.28 |
| R2 | 0.99 | 0.99 | 0.99 | 0.99 |  | 0.99 |

Example 5 miRNA Spiking and Recovery Test from a Plasma Sample

A mixture of Let-7a-f miRNAs was spiked in plasma. The spiked plasma sample was serially diluted 10× with Hyb buffer. The miRNAs were captured and quantified by the beads and TaqMan PCR. Results are shown in FIG. 5.

Example 6

Capturing and Quantification of a Panel of 96 miRNAs Using Anti miRNA Beads

The following protocol was used. Dilute 5 µL fresh blood in 490 µL Hybridization Dilution buffer (ABI). Spike in 5 µL of 1 nM ath-miR159a RNA Artificial Template. Add anti miRNA beads prepared according to Example 2 with 96 anti miRNA oligonucleotides and shake at 1200 rpm for 20 min at room temperature to hybridize. Wash the beads with RNA Purification Wash Solution I and RNA Purification Wash Solution II as described previously. Add elution buffer and vortex to mix. Heat bead elution sample in 70° C. for 2 minutes and then place immediately on ice. Perform reverse transcription and TaqMan real-time PCR as described in Example 4. The quantitative real-time PCR Ct profiles are shown in FIG. 6A. A similar experiment is conducted on 50 microL of human plasma. The results are presented in FIG. 6B. miRNA detectability and reproducibility was further confirmed as shown in FIG. 9 and the table below:

|  | Run 1 | Run 2 |
|---|---|---|
| Total miRNA Tested | 96 | 96 |
| Detectable miRNA (Ct <35) | 71 | 70 |
| Undetectable miRNA | 25 | 26 |
| Detection Rate | 74.0% | 72.9% |

Example 7 miRNA capturing and quantification from saliva. The following protocol was used.

Collect about 200 µL saliva and centrifuge briefly. Take 100 µL of the centrifuged saliva and add to 196 µL Hybridization buffer. Vortex vigorously for 30 seconds. Spike in 4 µL of 1 nM ath-miR159a RNA Artificial Template. This is Sample E. Dilute Sample E serially according to following table using Hybridization buffer.

| Hyb Sample | Hyb Dilution buffer µL | Stock Sample and Volume | Total Volume µL | Saliva Input nL/100 µL |
|---|---|---|---|---|
| E |  | Prepared in step 1 |  | 33300 |
| D | 135 | E: 15 µL | 150 | 3330 |
| C | 135 | D: 15 µL | 150 | 333 |
| B | 135 | C: 15 µL | 150 | 33.3 |
| A | 135 | B: 15 µL | 150 | 3.33 |

Add anti miRNA beads to Hyb Samples A, B, C, D, and E prepared above. Shake the hybridization samples in tubes at 1200 rpm for 20 min at room temperature. Wash the beads with RNA Purification Wash Solution I and RNA Purification Wash Solution II as described previously. Add elution buffer and vortex to mix. Heat bead elution sample in 70° C. for 2 minutes and then place immediately on ice. Perform reverse transcription and TaqMan real-time PCR as described in Example 4. The quantitative real-time PCR Ct profiles are shown in table below and in FIG. 7.

|  | Let-7a | Let-7b | Let-7c | Let-7d | Let-7e | Let-7f | ath-159a | miR320 |
|---|---|---|---|---|---|---|---|---|
| NTC | 40.00 | 36.58 | 37.30 | 40.00 | 40.00 | 40.00 | 37.13 | 40.00 |
| 3 nL | 34.65 | 33.11 | 35.49 | 38.60 | 40.00 | 37.15 | 29.54 | 34.09 |
| 30 nL | 31.84 | 32.13 | 34.83 | 38.60 | 40.00 | 35.43 | 27.25 | 34.24 |
| 300 nL | 29.44 | 29.77 | 31.80 | 34.09 | 40.00 | 34.13 | 23.75 | 34.04 |
| 3000 nL | 26.97 | 26.93 | 29.93 | 30.52 | 36.23 | 30.08 | 20.33 | 31.45 |
| 30000 nL | 24.03 | 24.07 | 26.96 | 27.67 | 33.80 | 27.50 | 17.04 | 28.66 |

Example 8

Protocols for miRNA Detection and Profiling Using Anti-Probe Beads

Two anti-miRNA bead Panels: A384C6: beads with 386 miRNA targets based on the ABI Megaplex A assay panel. B384C6: beads with 385 miRNA targets based on the ABI Megaplex B assay panel.

None-Human miRNA Controls: Each panel contains 6 non-human miRNAs: ath-miR159a, cel-miR-2, cel-miR-39, cel-miR-54, cel-miR-238, cel-lin-4. They can be used as external controls at user's choice.

Reagents in the kit: Lysis Buffer, ABC Buffer, Wash Buffer 1, Wash Buffer 2, Elution Buffer, LoBind Tubes (Eppendorf), Human Panel A Beads (1 million/microL). Or Human Panel Panel B Beads.

Reagent Preparation: Add 6 mL of Lysis Buffer to the ABC Buffer bottle to make the final ABC Buffer for use. Add 7 mL of 100% Ethanol to the Wash Buffer 2 bottle to make the final Wash Buffer 2 for use.

Reagents required: TaqMan® MicroRNA Reverse Transcription Kit (ABI PN: 4366597), TaqMan® MicroRNA Assays (ABI PN: 4427975), TaqMan® Universal Master Mix II (ABI PN: 4440040)

miRNA Purification

Beads Preparation: Vortex the beads thoroughly to suspend the beads in solution. Sonicate the beads by an ultrasonic water bath for 1 minute. Vortex and then aliquot 80 uL beads (80 million beads total) into a LoBind 1.5-mL microfuge tube. Magnet the beads for 1 minute and remove the supernatant.

Sample Preparation: Select (check mark) the sample type you are going to test. Based on your selection, prepare the sample for hybridization according to following procedures:

| Sample Type | Sample Amount | Preparation |
| --- | --- | --- |
| Whole Blood | 10 uL | Mix 10 uL whole blood with 20 uL Lysis Buffer and vortex for ~30 seconds. Add 120 uL ABC Buffer and vortex for ~30 seconds. Total volume ~150 uL |
| Blood Lysate | 30 uL | Dilute 30 uL blood lysate with 120 uL ABC Buffer and vortex. Total volume ~150 uL |
| Plasma | 50 uL | Mix 50 uL plasma with 100 uL ABC Buffer and vortex for ~30 seconds. Total volume ~150 uL |
| Serum | 50 uL | Mix 50 uL serum with 100 uL ABC Buffer and vortex for ~30 seconds. Total volume ~150 uL |
| Cell Cultures | 5 × 10^4 cells in 50 uL PBS | Mix the 50 uL cell/PBS suspension with 150 uL Lysis Buffer and vortex for ~30 seconds. Total volume ~200 uL |
| Solid Tissue | 1-10 mg | If needed, grind or homogenize the tissue. Add 30 uL Lysis Buffer and vortex for ~30 seconds. Add 120 uL ABC Buffer and vortex for ~30 seconds. Total volume ~150 uL |
| FFPE | 1 dissection (5-10 um) | Wash the FFPE sample with xylene (2 min × 2), 100%, 95% and 75% ethanol (1 min each), H2O (1 min). Add 30 uL Lysis Buffer and vortex for ~30 seconds. Add 120 uL ABC Buffer and vortex for ~30 seconds. Total volume ~150 uL |
| Raw Milk | 100 uL | Mix 100 uL raw milk with 200 uL Lysis Buffer and vortex for ~30 seconds. Total volume ~300 uL |
| Saliva | 50 uL | Centrifuge 15 min at 2000 rpm to remove debris. Mix 50 uL saliva with 100 uL Lysis Buffer and vortex for ~30 seconds. Total volume ~150 uL |
| Urine | 50 uL | Centrifuge 15 min at 2000 rpm to remove debris. Mix 50 uL urine with 100 uL Lysis Buffer and vortex for ~30 seconds. Total volume ~150 uL |

(Optional) Spike in 2 uL of 1 nM external control miRNA (following six can be captured by the beads: ath-miR-159a, cel-miR-2, cel-miR-39, cel-miR-54, cel-miR-238, cel-Lin4) and vortex.

Hybridization: Transfer all the prepared sample into the bead tube prepared above. Using a ThermoMixer, shake the vial at 1200 rpm at 30° C. for 40 minutes.

Wash: Magnet the beads for 1 minute and remove the supernatant. Add 100 uL Wash Buffer 1. Vortex to resuspend the beads into solution then pulse briefly. Magnet the beads for 1 minute and remove the supernatant. Add 100 uL Wash Buffer 2. Vortex briefly to resuspend the beads into solution then pulse briefly. Magnet the beads for 1 minute and remove the supernatant. Repeat step c. Pulse the tube down to collect any residual liquid. Place the tube on magnetic rack for 20 sec, and remove any residual liquid using a fine pipette tip.

Elution: Add 100 uL Elution Buffer and vortex to mix then pulse briefly. Using a ThermoMixer, shake the tube at 1200 rpm at 70° C. for 3 minutes then place it immediately on the magnetic stand for 1 minute. Carefully transfer the supernatant (miRNA sample) into a clean LoBind tube. (Optional—this dilution step is only for a full 96-well plate run. The concentrated sample can be directly used). Add 500 uL H2O to dilute the sample (total volume ~600 uL). Place the sample vial on ice. Store the miRNA sample at −80° C. if not used immediately.

Reverse Transcription Reaction

Following operations are for a panel of 96 miRNA assays in a 96-well plate. Aliquot each 5× RT primer into a 96-well PCR plate, 3 uL per assay per well. Prepare miRNA RT mix:

| Component | Stock | Volume: 1 Reaction | Volume: 100 Reactions |
| --- | --- | --- | --- |
| Nuclease-free dH$_2$O | | 4.16 | 416 |
| 25 mM each (100 mM total) dNTPs | 25 mM | 0.15 | 15 |
| 50X MultiScribe Reverse Transcriptase | 50X | 1.0 | 100 |

-continued

| Component | Stock | Volume: 1 Reaction | Volume: 100 Reactions |
| --- | --- | --- | --- |
| 10X RT Buffer | 10X | 1.5 | 150 |
| 20 U/uL AB RNase Inhibitor | 20 U/uL | 0.19 | 19 |
| Total | | 7.0 | 700 |

Pipette 7 uL miRNA RT mix to each well of the RT plate prepared above. Add 5 uL miRNA sample to each well (final total RT volume 15 uL/well). Cover the plate with Heavy-Duty sealing film, mix, and centrifuge. Incubate at 16° C./30 min, 42° C./30 min, 85° C./5 min, 4° C. hold. Store at −20° C.

TAQMAN PCR Reaction

Following operations are for a panel of 96 miRNA assays in a 96-well plate. Aliquot 20× TaqMan miRNA assays into a 96-well PCR plate, 1 uL per assay per well. Each miRNA assay location should match the corresponding RT plate location. Prepare TaqMan PCR mix.

| Component | Stock | Volume (uL): 1 reaction | Volume (uL): 100 reaction |
| --- | --- | --- | --- |
| Nuclease-free dH$_2$O | | 7 | 700 |
| 2X Universal Master Mix II | 2X | 10 | 1000 |
| Total | | 17 | 1700 |

Pipette the PCR mix to each well, 17 uL/well. Transfer 2 uL RT reaction solution obtained from the RT step into corresponding well location of the TaqMan plate. Total reaction volume 20 uL. Run PCR: 95° C./10 min, 95° C./15 sec & 60° C./60 sec for 40 cycles, Set FAM as reporter dye with ROX as Reference.

Representative results from various tissues, body fluids, cancer cell lines, breast cancer formalin-fixed paraffin-embedded (FFPE) samples, among others are shown in figures XX-XX and tables below. The miRNAs are isolated from various tissues using Laser Capture Microdissection (LCM) technique.

miRNA Profiling from Human Bladder LCM Samples

| LCM Diameter | Area, um2 | Log(Area) | hsa-Let-7a | hsa-Let-7c | hsa-miR-16 | hsa-miR-320 | hsa-miR-92a |
|---|---|---|---|---|---|---|---|
| NTC | 0 | | 40.00 | 40.00 | 38.27 | 37.39 | 40.00 |
| 100 um | 7850 | 3.8949 | 35.34 | 37.56 | 34.20 | 35.61 | 40.00 |
| 200 um | 31400 | 4.4969 | 33.19 | 35.52 | 31.68 | 35.50 | 40.00 |
| 1000 um | 785000 | 5.8949 | 27.16 | 31.17 | 28.03 | 33.28 | 40.00 |

Example 9 microRNA Profiling from Urine

The profiling of microRNA in human urine samples during pregnancy at various stages of pregnancy showed that of the 384 miRNAs tested, 200 were detected in Urine samples using a Ct cutoff of 35. 18 pregnancy related miRNAs consistently showed increased expression with pregnancy progression to second trimester.

Expression of miR143 and miR145 in urine for patients with balloon injured artery and normal individuals was compared. miR143 and miR145 are significantly down regulated in balloon injured arteries in comparison to normal artery. The results are shown in the table below. A representative miRNA profiling is shown in FIG. 17.

| Assay ID | Workflow | Sample ID# | Avg.CY | StDev Ct |
|---|---|---|---|---|
| miR-143 | Indy | Normal | 35.72 | 1.06 |
| miR-143 | Indy | Stent Artery | 48.66 | 1.9 |
| miR-143 | TiLDA | Normal | 33.08 | 0.06 |
| miR-143 | TiLDA | Stent Artery | 39.61 | 0.55 |
| miR-145 | Indy | Normal | 36.5 | 1.63 |
| miR-145 | Indy | Stent Artery | 48.09 | 1.69 |
| miR-145 | TiLDA | Normal | 30.73 | 0.32 |
| miR-145 | TiLDA | Stent Artery | 36.84 | 0.53 |

All references cited within this disclosure are hereby incorporated by reference in their entirety. While certain embodiments have been described in terms of the preferred embodiments, it is understood that variations and modifications will occur to those skilled in the art. Therefore, it is intended that the appended claims cover all such equivalent variations that come within the scope of the following claims.

---

---

The invention claimed is:

1. A method for isolating a multiplicity of miRNA targets from a sample, comprising:
   a) contacting the sample with a lysis buffer to form a sample lysate;
   b) contacting the sample lysate with a bead covalently attached to a multiplicity of anti-miRNA probes to form a sample lysate-bead mixture, wherein each of the multiplicity of anti-miRNA probes is configured to selectively hybridize to a different species of the multiplicity of miRNA targets such that each bead comprises a mixture of a multiplicity of different anti-miRNA probe sequences, and wherein each of the multiplicity of anti-miRNA probes is single-stranded and comprises a nucleotide hybridizing portion having complementarity to one of the multiplicity of miRNA targets and a nucleotide linker binding portion for attachment to the bead;

c) incubating the sample lysate-bead mixture to form a hybridized complex between at least one of the multiplicity of miRNA targets and at least one of the multiplicity of anti-miRNA probes;

d) washing the lysate-bead mixture of step (c) to remove unbound sample lysate material; and e) eluting the hybridized complex to form an elution sample comprising at least one of the multiplicity of miRNA targets.

2. The method according to claim 1, wherein the bead is a magnetic bead.

3. The method according to claim 2, wherein the bead is carboxylic acid functionalized bead.

4. The method according to claim 1, wherein the one or more of the multiplicity of anti-miRNA probes is covalently attached to the bead by ligation of the nucleotide linker binding portion to a bead comprising a DNA molecule (i.e., a DNA bead).

5. The method according to claim 4, wherein the one or more of the multiplicity of anti-miRNA probes is ligated to the DNA molecule using a single-strand DNA ligase.

6. The method according to claim 1, wherein the multiplicity of anti-miRNA probes are covalently attached to the bead using a chemical synthesis reaction.

7. The method according to claim 1, wherein the multiplicity of anti-miRNA probes are covalently attached to the bead using an enzymatic synthesis reaction.

8. The method according to claim 7, wherein enzymatic synthesis reaction comprises a ligation reaction.

9. The method according to claim 1, wherein the sample is selected from the group consisting of blood, serum, plasma, urine, saliva, cerebrospinal fluid, wound exudates, biopsies, autopsies, tissues, formalin-fixed, paraffin-embedded (PPFE) samples, and organs.

10. The method according to claim 1, further comprising a step for:
(f) identifying and/or quantifying the multiplicity of miRNA targets.

11. The method according to claim 10, wherein at least one of the multiplicity of miRNA targets is isolated from the bead before identifying and/or quantifying one or more of the multiplicity of miRNA targets.

12. The method according to claim 10, wherein the identifying and/or quantifying one or more of the multiplicity of miRNA targets comprises using reverse transcription followed by real-time (RT) or quantitative polymerase chain reaction (q-PCR).

13. The method according to claim 10, wherein the step for: (f) identifying and/or quantifying is carried out by TaqMan real time PCR.

14. The method of claim 1, wherein each of the multiplicity of anti-miRNA probes further comprises an additional nucleotides that is not part of the nucleotide hybridizing portion or the nucleotide linker portion.

15. The method according to claim 14, wherein the additional nucleotide comprises a 3'-dideoxynucleotide.

16. The method of claim 1, wherein the nucleotide linker binding portion is at the 5'-end of each of the multiplicity of anti-miRNA probes.

17. The method according to claim 16, wherein the nucleotide linker binding portion comprise a 5'-phosphate group.

* * * * *